US012766505B2

(12) United States Patent
Yazawa

(10) Patent No.: US 12,766,505 B2
(45) Date of Patent: Oct. 20, 2026

(54) MICROFLUIDIC CHIPS AND METHODS OF PRODUCING MICROFLUIDIC CHIPS

(71) Applicant: TOPPAN HOLDINGS INC., Tokyo (JP)

(72) Inventor: Hiroko Yazawa, Taito-ku (JP)

(73) Assignee: TOPPAN HOLDINGS INC., Tokyo (JP)

( * ) Notice: Subject to any disclaimer, the term of this patent is extended or adjusted under 35 U.S.C. 154(b) by 279 days.

(21) Appl. No.: 18/756,815

(22) Filed: Jun. 27, 2024

(65) Prior Publication Data

US 2024/0351024 A1 Oct. 24, 2024

Related U.S. Application Data

(63) Continuation of application No. PCT/JP2022/047767, filed on Dec. 23, 2022.

(30) Foreign Application Priority Data

Dec. 28, 2021 (JP) ................................ 2021-214522

(51) Int. Cl.
*B01L 3/00* (2006.01)
*G01N 33/483* (2006.01)
(Continued)

(52) U.S. Cl.
CPC ... *B01L 3/502707* (2013.01); *B01L 3/502715* (2013.01); *B01L 3/502723* (2013.01);
(Continued)

(58) Field of Classification Search
CPC ......... B01L 3/502707; B01L 3/502715; B01L 3/502723; B01L 2200/0684;
(Continued)

(56) References Cited

U.S. PATENT DOCUMENTS 6,762,057 B1 * 7/2004 Gilton .............. G01N 27/44791 210/207
8,246,832 B2 * 8/2012 Lomas ................. G01N 30/461 210/638

(Continued)

FOREIGN PATENT DOCUMENTS

JP 3597995 B2 12/2004
JP 2006-223118 A 8/2006

(Continued)

OTHER PUBLICATIONS

International Search Report issued Mar. 28, 2023 in PCT/JP2022/047767, filed Dec. 23, 2022, 5 pages.

(Continued)

*Primary Examiner* — Minh Q Le
(74) *Attorney, Agent, or Firm* — Oblon, McClelland, Maier & Neustadt, L.L.P.

(57) ABSTRACT

A microfluidic chip includes a fluidic channel portion, a cover layer, a substrate, and partition layers interposed between the cover layer and the substrate to define the fluidic channel portion. The partition layer has a curved portion curved away from the cover layer at an edge on the fluidic channel portion side of an upper contact surface in contact with the cover layer, and the fluidic channel portion includes a bubble trapping region formed by the curved portion and a rear surface of the cover layer on the fluidic channel portion side. The bubble trapping region traps air bubbles in the fluidic channel portion.

20 Claims, 13 Drawing Sheets

(51) Int. Cl.
*G01N 33/487* (2006.01)
*G01N 33/49* (2006.01)
*G01N 35/08* (2006.01)

(52) U.S. Cl.
CPC ... *B01L 2200/0684* (2013.01); *B01L 2200/12* (2013.01); *B01L 2300/0816* (2013.01); *B01L 2300/0887* (2013.01); *B01L 2400/086* (2013.01); *G01N 33/4833* (2013.01); *G01N 33/48707* (2013.01); *G01N 33/49* (2013.01); *G01N 35/08* (2013.01)

(58) Field of Classification Search
CPC ......... B01L 2200/12; B01L 2300/0816; B01L 2300/0887; B01L 2400/086; G01N 33/4833; G01N 33/49; G01N 33/48707; G01N 35/08
USPC ............ 137/1; 422/502, 503, 70; 210/198.2, 210/741, 137, 656, 808; 436/52, 161, 436/162
See application file for complete search history.

(56) References Cited

U.S. PATENT DOCUMENTS 9,101,934 B2 8/2015 Kitamoto
2003/0150555 A1* 8/2003 Gandhi .................. B29C 65/08 156/308.2
2003/0226604 A1* 12/2003 Schlautmann .... B01L 3/502707 137/827
2004/0238052 A1* 12/2004 Karp .................... B01J 19/0093 137/822
2006/0199260 A1* 9/2006 Zhang .................... C12M 23/34 435/293.1
2007/0254278 A1* 11/2007 DeSimone ......... C08G 18/5015 428/305.5
2008/0317632 A1 12/2008 Shimasaki et al.
2014/0027005 A1* 1/2014 Li .......................... F16L 9/006 138/177
2016/0136638 A1 5/2016 Hieda et al.
2020/0298232 A1* 9/2020 Madadi ............. B01L 3/502707
2024/0342706 A1* 10/2024 Yazawa ............. B01L 3/502723
2024/0351025 A1* 10/2024 Yazawa ..................... B81C 1/00

FOREIGN PATENT DOCUMENTS

JP 2006-242607 A 9/2006
JP 2007-240461 A 9/2007
JP 2014-097485 A 5/2014
WO WO 2015/012212 A1 1/2015

OTHER PUBLICATIONS

Extended European Search Report Issued Apr. 14, 2025 in European Application No. 22915982.7, 10 pages.

* cited by examiner

MICROFLUIDIC CHIPS AND METHODS OF PRODUCING MICROFLUIDIC CHIPS

CROSS-REFERENCE TO RELATED APPLICATIONS

The present application is a continuation of and claims the benefit of priority to International Application No. PCT/JP2022/047767, filed Dec. 23, 2022, which is based upon and claims the benefit of priority to Japanese Application No. 2021-214522, filed Dec. 28, 2021. The entire contents of these applications are incorporated herein by reference.

BACKGROUND OF THE INVENTION

Field of the Invention

The present invention relates to microfluidic chips and methods of producing the same.

Description of Background Art

JP 2006-223118 A describes a method of removing air bubbles from the micro fluidic channel. Further, JP 2007-240461 A describes a method of producing a microfluidic chip by bonding components together with an adhesive. The entire contents of these publications are incorporated herein by reference.

SUMMARY OF THE INVENTION

According to one aspect of the present invention, a microfluidic chip includes a first support member, a second support member, and partition members interposed between the first support member and the second support member such that the first support member, the second support member and the partition members form a fluidic channel. Each of the partition members has an curved portion curved away from the first support member at an edge on a fluidic channel side of a contact surface in contact with the first support member such that the curved portion and a surface of the first support member on the fluidic channel side form a bubble trapping region that traps air bubbles in the fluidic channel.

According to another aspect of the present invention, a method of producing a microfluidic chip includes applying a resin to a substrate, exposing the resin applied to the substrate to light, subjecting the resin to development and cleaning such that partition members and a fluidic channel are formed on the substrate, post-baking the partition members formed on the substrate, and bonding a cover layer to a side of the partition members on the opposite side with respect to the substrate. The subjecting the resin to the development and cleaning includes removing excess resin on the substrate such that an upper curved portion curved in a convex shape is formed at an edge on a fluidic channel side of a surface of each of the partition members on the opposite side with respect to the substrate.

According to yet another aspect of the present invention, a method of producing a microfluidic chip includes applying a resin to a substrate, exposing the resin applied to the substrate to light, subjecting the resin to development and cleaning such that partition members and a fluidic channel are formed on the substrate, post-baking the partition members formed on the substrate, and bonding a cover layer to a side of the partition members on the opposite side with respect to the substrate. The subjecting the resin to the development and cleaning includes removing excess resin on the substrate such that a curved portion curved in a convex shape is formed at an edge on a fluidic channel side of a surface of each of the partition members in contact with the substrate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
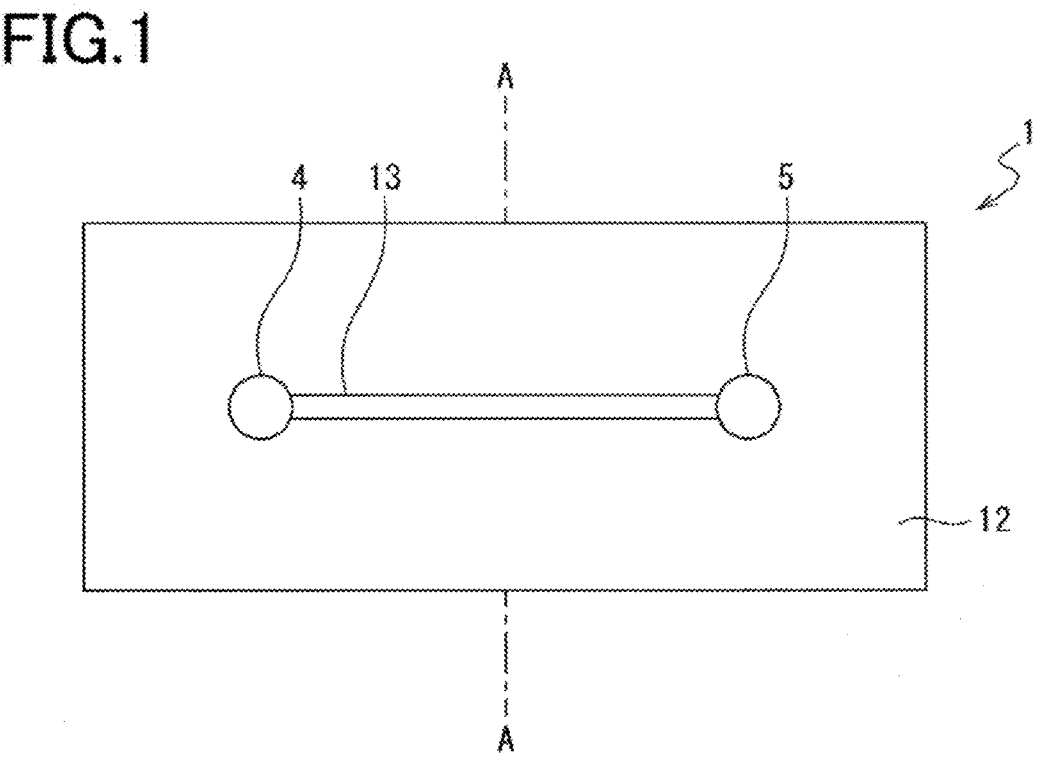
FIG. 1 is a schematic plan view illustrating an example configuration of a microfluidic chip according to a first embodiment of the present invention.

Embodiments will now be described with reference to the accompanying drawings, wherein like reference numerals designate corresponding or identical elements throughout the various drawings.

In the following description, a substrate side of a microfluidic chip may be referred to as "lower side", and a side (lid material side) of the microfluidic chip opposite to that facing the substrate may be referred to as "upper side".

In microfluidic chips, a region (bubble trapping region) for trapping air bubbles in a fluidic channel can be formed by providing a wall with a specific shape. Accordingly, a microfluidic chip according to an embodiment of the present invention separates air bubbles in a micro fluidic channel into a specific region to improve stability of fluid flow and prevents an adhesive component from eluting into a solution in the fluidic channel to suppress inhibition of reaction of the solution, and a method of producing the microfluidic chip.

First Embodiment

Basic Configuration of Microfluidic Chip

Figure 2:
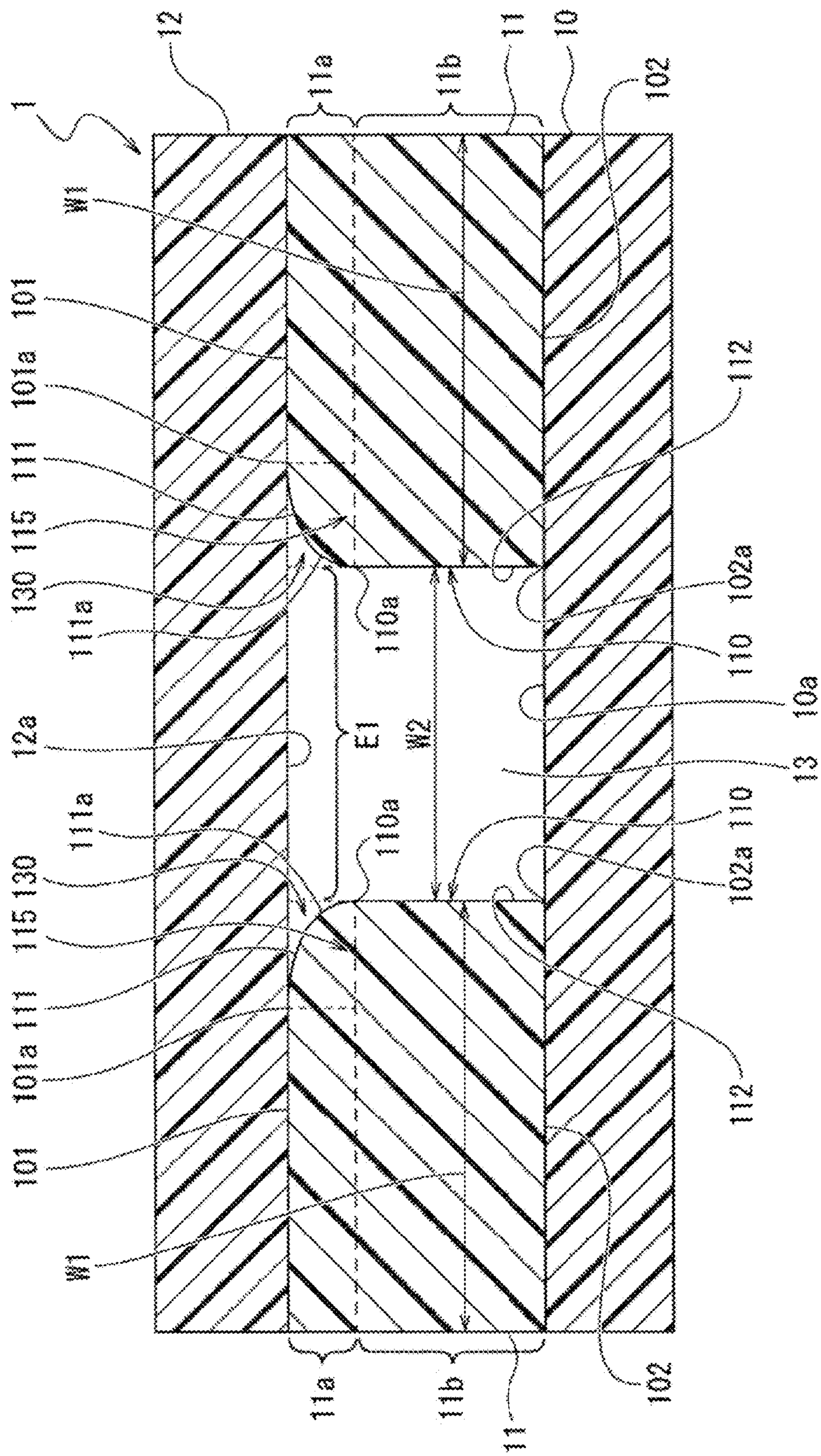
FIG. 2 is a schematic cross-sectional diagram illustrating an example configuration of a microfluidic chip according to the first embodiment of the present invention.

FIGS. 1 and 2 are schematic diagrams illustrating an example configuration of a microfluidic chip 1 according to a first embodiment of the present invention (hereinafter, also referred to as "the present embodiment"). Specifically, FIG. 1 is a schematic plan view of the microfluidic chip 1 of the present embodiment. FIG. 2 is a schematic cross-sectional diagram illustrating a cross-section of the microfluidic chip 1 taken along the line A-A shown in FIG. 1.

As shown in FIG. 1, the microfluidic chip 1 includes an inlet 4 for introducing a fluid (for example, liquid), a fluidic channel portion 13 through which the fluid introduced through the inlet 4 flows, and an outlet 5 for discharging the fluid from the fluidic channel portion 13. In the microfluidic chip 1, the fluidic channel portion 13 is covered with a cover layer 12, and the inlet 4 and the outlet 5 are through holes formed in the cover layer 12. Details of the cover layer 12 will be described later.

FIG. 1 shows the fluidic channel portion 13 as seen through the transparent cover layer 12.

In the microfluidic chip 1, at least one inlet 4 and at least one outlet 5 may be provided, and multiple of each may be provided. Further, in the microfluidic chip 1, multiple fluidic channel portions 13 may be provided, and the fluidic channel portions 13 may be designed to merge or branch the fluid introduced from the inlet 4.

In the following description, details of the members constituting the fluidic channel portion 13 in the microfluidic chip 1 will be described. As shown in FIG. 2, in the microfluidic chip 1, the fluidic channel portion 13, which is a fluidic channel through which a fluid flows, is defined by walls sandwiched between two support members (first and second support members). In this example, the cover layer 12 provided on the upper side of the partition layer 11 to cover the upper part of the fluidic channel portion 13 corresponds to the first support member, and the substrate 10 provided on the bottom side of the partition layer 11 to form the bottom of the fluidic channel portion 13 corresponds to the second support member. That is, the microfluidic chip 1 includes the fluidic channel portion 13, the cover layer (an example of first support member) 12, the substrate (an example of second support member) 10, and a pair of partition layers (an example of partition member) 11 interposed between the cover layer 12 and the substrate 10 to define the fluidic channel portion 13.

The fluidic channel portion 13 through which the fluid introduced from the inlet 4 flows is a region surrounded by the substrate 10, the partition layer 11 and the cover layer 12. The fluidic channel portion 13 is defined by a pair of partition layers 11 facing each other on the substrate 10, and a side of the fluidic channel portion 13 opposite to that facing the substrate 10 is covered with the cover layer 12 as a lid material. As described above, a fluid is introduced into the fluidic channel portion 13 from the inlet 4 (see FIG. 1) formed in the cover layer 12, and the fluid that has flowed through the fluidic channel portion 13 is discharged from the outlet 5.

Although details will be described later, in the microfluidic chip 1 according to the present embodiment, the partition layer 11 has a curved portion 115 curved away from the cover layer 12 at an edge 101*a* on the fluidic channel portion 13 side of an upper contact surface 101 in contact with the cover layer 12. Further, the fluidic channel portion 13 includes a bubble trapping region 130 formed by the curved portion 115 and a rear surface 12*a* which is a surface of the cover layer 12 on the fluidic channel portion 13 side, and the bubble trapping region 130 traps air bubbles in the fluidic channel portion 13.

As shown in FIG. 2, the bubble trapping region 130 is formed by providing the partition layer 11 with a specific shape, that is, by providing the partition layer 11 with the curved portion 115, and not by attaching a separate member with an adhesive. With this configuration, the microfluidic chip 1 can separate air bubbles in the fluidic channel portion 13 into the bubble trapping region 130 to improve stability of fluid flow, and prevent elution of an adhesive component into a solution in the fluidic channel to suppress inhibition of reaction of the solution.

Substrate

The substrate 10 is a member that serves as a base of the microfluidic chip 1, and the partition layer 11 provided on the substrate 10 defines the fluidic channel portion 13. That is, the substrate 10 and the partition layer 11 can be regarded as a main body of the microfluidic chip 1.

The substrate 10 can be made of either a translucent material or a non-translucent material. For example, when the state inside the fluidic channel portion 13 (state of fluid) is detected and observed using light, a material having excellent transparency to the light can be used. As the translucent material, resin, glass, or the like can be used. Examples of the resin used for the translucent material constituting the substrate 10 include acrylic resin, methacrylic resin, polypropylene, polycarbonate resin, cycloolefin resin, polystyrene resin, polyester resin, urethane resin, silicone resin and fluororesin from the viewpoint of being suitable for forming the main body of the microfluidic chip 1.

Further, for example, when the state inside the fluidic channel portion 13 (state of fluid) does not have to be detected and observed using light, a non-translucent material may be used. Examples of the non-translucent material include silicon wafers and copper plates. Although the thickness of the substrate 10 is not particularly limited, it is preferably in the range of 10 μm (0.01 mm) or greater and 10 mm or less since a certain degree of rigidity is required in the formation of a fluidic channel.

Partition Layer

The partition layer 11 is disposed on the substrate 10 and defines the fluidic channel portion 13. The partition layer 11 can be made of a resin material. Examples of the resin material of the partition layer 11 include a photosensitive resin.

The photosensitive resin constituting the partition layer 11 is preferably photosensitive to light having a wavelength of 190 nm or greater and 400 nm or less, which is in the ultraviolet light region. As the photosensitive resin, a photoresist such as liquid resist or dry film resist can be used. The photosensitive resin may be either positive type in which the photosensitive region dissolves or negative type in which the photosensitive region becomes insoluble.

Examples of the photosensitive resin composition suitable for forming the partition layer 11 in the microfluidic chip 1 include radical negative type photosensitive resins containing alkali-soluble polymers, addition polymerizable monomers and photopolymerization initiators. Examples of the photosensitive resin material include acrylic resins, acrylic urethane resins (urethane acrylate resins), epoxy resins, polyamide resins, polyimide resins, polyurethane resins, polyester resins, polyether resins, polyolefin resins, polycarbonate resins, polystyrene resins, norbornene resins, phenol novolac resins, and other photosensitive resins, and these can be used singly, or in combinations or as copolymers of two or more.

In the present embodiment, the resin material of the partition layer 11 is not limited to a photosensitive resin, and may be, for example, silicone rubber (PDMS: polydimethylsiloxane) or synthetic resin. Examples of the synthetic resin include polymethyl methacrylate resin (PMMA), polycarbonate (PC), polystyrene resin (PS), polypropylene (PP), cycloolefin polymer (COP) and cycloolefin copolymer (COC). The resin material of the partition layer 11 is preferably selected as appropriate according to the application.

Further, the thickness of the partition layer 11 on the substrate 10, that is, the height of the fluidic channel portion 13, is not particularly limited, but is greater than the substances to be analyzed or inspected (for example, drugs, bacteria, cells, red blood cells, leukocytes, etc.) contained in the fluid introduced into the fluidic channel portion 13. Therefore, the thickness of the partition layer 11, that is, the height of the fluidic channel portion 13, is preferably in the range of 5 μm or greater and 100 μm or less.

Similarly, since the width of the fluidic channel portion 13 is greater than the substances to be analyzed or inspected, the width of the fluidic channel portion 13 defined by the partition layer 11 is preferably in the range of 5 μm or greater and 100 μm or less.

Further, in order to ensure sufficient reaction time for the reaction solution, the length of the fluidic channel defined by the partition layer 11 is preferably in the range of 10 mm or greater and 100 mm or less, more preferably in the range of 30 mm or greater and 70 mm or less, and still more preferably in the range of 40 mm or greater and 60 mm or less.

Cover Layer

In the microfluidic chip 1 of the present embodiment, the cover layer 12 is disposed on a side of the partition layer 11 opposite to that facing the substrate 10, covering the fluidic channel portion 13 as shown in FIG. 2. As described above, the cover layer 12, disposed on a side of the partition layer 11 opposite to that facing the substrate 10, faces the substrate 10 with the partition layer 11 therebetween. More specifically, as shown in FIG. 2, the cover layer 12 in cross-sectional view has side portions supported by the partition layer 11 and a center region that faces the substrate 10, the center region defining the upper side of the fluidic channel portion 13.

The cover layer 12 can be made of either a translucent material or a non-translucent material. For example, when the state inside the fluidic channel is detected and observed using light, a material having excellent transparency to the light can be used. As the translucent material, resin, glass, or the like can be used. Examples of the resin constituting the cover layer 12 include acrylic resin, methacrylic resin, polypropylene, polycarbonate resin, cycloolefin resin, polystyrene resin, polyester resin, urethane resin, silicone resin and fluororesin from the viewpoint of being suitable for forming the main body of the microfluidic chip 1. The thickness of the cover layer 12 is not particularly limited, but in view of forming through holes corresponding to the inlet 4 and the outlet 5 in the cover layer 12, it is preferably in the range of 10 μm or greater and 10 mm or less. Further, it is also preferred that holes corresponding to the inlet 4 for introducing a fluid (liquid) and the outlet 5 for discharging a fluid are formed in advance in the cover layer 12 before the cover layer 12 is bonded to the partition layer 11.

Shape of Partition Layer and Configuration of Fluidic Channel

In the following description, details of the shape of the partition layer 11 and the configuration of the fluidic channel portion 13 in the microfluidic chip 1 according to the present embodiment will be described. First, the shape of the partition layer 11 that defines the fluidic channel portion 13 will be described.

Shape of Partition Layer and Configuration of Fluidic Channel

In the following description, details of the shape of the partition layer 11 and the configuration of the fluidic channel portion 13 in the microfluidic chip 1 according to the present embodiment will be described. First, the shape of the partition layer 11 that defines the fluidic channel portion 13 will be described.

As shown in FIG. 2, the partition layer 11 of the microfluidic chip 1 has a curved portion 115 curved away from the first support member (cover layer 12) at the edge 101*a* on the fluidic channel side of the upper contact surface 101 in contact with the cover layer 12. Further, the fluidic channel portion 13 includes the bubble trapping region 130 formed by the partition layer 11 (specifically, the curved portion 115) and a surface of the first support member (cover layer 12) on the fluidic channel portion 13 side (rear surface 12*a*), and the bubble trapping region 130 traps air bubbles in the fluidic channel portion 13. With this configuration, the microfluidic chip 1 can separate air bubbles in the fluidic channel portion 13 into a specific region to improve stability of fluid flow. Further, the bubble trapping region 130 is not provided by attaching a separate member with an adhesive but is provided by forming the partition layer 11 into a specific shape (by forming the curved portion 115). With this configuration, the microfluidic chip 1 can prevent elution of an adhesive component into a solution in the fluidic channel to suppress inhibition of reaction of the solution. In the following description, the shape of the partition layer 11 will be more specifically described.

As shown in FIG. 2, the partition layer 11 of the microfluidic chip 1 includes the upper contact surface 101, a lower contact surface 102 and a side surface 110.

The upper contact surface 101 is the top of the partition layer 11, and a surface where the partition layer 11 is contact with the cover layer 12. Further, the lower contact surface 102 is the bottom of the partition layer 11, and a surface where the partition layer 11 is in contact with the substrate 10. That is, the partition layer 11 is adhered (bonded) to the cover layer 12 at the upper contact surface 101 and adhered (bonded) to the substrate 10 at the lower contact surface 102.

The side surface 110 is the side surface of the partition layer 11, and a surface defining the fluidic channel portion 13. The side surface 110 extends from the edge 101*a* of the upper contact surface 101 of the partition layer 11 to the edge 102*a* of the lower contact surface and is connected to the cover layer 12 at the edge 101*a* and to the substrate 10 at the edge 102*a*. That is, the edge 101*a* corresponds to the upper end of the side surface 110, and the edge 102*a* corresponds to the lower end of the side surface 110.

A curved surface 111 which is a curved inclined surface is provided on one end side of the side surface 110. Specifically, the curved surface 111 is provided on the edge 101*a* side, which is the upper end side of the side surface 110.

On the other hand, no curved surface is provided on the other end side, which is the lower end (edge 102*a*) side of the side surface 110. That is, in the side surface 110, the curved surface 111 does not include the lower end (edge 102*a*). In the side surface 110, a flat surface 112 is provided in a region where the curved surface 111 is not provided.

The flat surface 112 is connected to the substrate 10 at the edge 102*a* (lower end of the side surface 110) of the partition layer 11 and connected to the curved surface 111 at an intermediate end 110*a* located between the edge 101*a* (upper end of the side surface 110) of the partition layer 11 and the edge 102*a* (lower end of the side surface 110).

That is, the lower end (edge 102*a*) of the side surface 110 corresponds to the lower end of the flat surface 112, and the intermediate end 110*a* corresponds to the upper end of the flat surface 112. Further, the intermediate end 110*a* of the side surface 110 corresponds to the lower end of the curved surface 111, and the upper end of the side surface 110 (edge 101*a*) corresponds to the upper end of the curved surface 111.

Hereinafter, a region of the partition layer 11 including the curved surface 111 (region including the curved portion 115 having the curved surface 111) is referred to as an upper region 11*a*, and a region including the flat surface 112 is referred to as a lower region 11*b*. In FIG. 2, the upper region 11*a* and the lower region 11*b* of the partition layer 11 are divided by a virtual dotted line for ease of understanding. In the partition layer 11, the upper region 11*a* and the lower region 11*b* are preferably formed integrally but may be formed separately. That is, the partition layer 11 may have a multilayer (e.g., two-layer) structure.

The partition layer 11 has a width W1 which is constant throughout the lower region 11*b* including the flat surface 112 and decreases toward the cover layer 12 in the upper region 11*a* including the curved surface 111. Accordingly, the area of the upper contact surface 101 in the partition layer 11 is smaller than the area of the lower contact surface 102. That is, the area of the bonding region for bonding the partition layer 11 and the cover layer 12 is smaller than the area of the bonding region for bonding the partition layer 11 and the substrate 10.

Therefore, in the microfluidic chip 1, the width of the fluidic channel portion 13 (fluidic channel width W2) increases toward the cover layer 12, which is the first support member, in a region formed by the curved portion 115 having the curved surface 111 in the partition layer 11. Further, the fluidic channel width W2 is constant in a region formed by a portion other than the curved surface 111 of the partition layer 11 (in this example, flat surface 112). With this configuration, the microfluidic chip 1 can ensure a region for forming the bubble trapping region 130 in the fluidic channel portion 13. Details of the fluidic channel width W2 of the fluidic channel portion 13 and the bubble trapping region 130 will be described later.

In the present embodiment, although the area of the upper contact surface 101 of the partition layer 11 is smaller than the area of the lower contact surface 102, it is sufficient to maintain adhesion between the partition layer 11 and the cover layer 12 in bonding these together and prevent occurrence of liquid leakage, damage, and the like during use of the microfluidic chip 1.

Next, the curved surface 111 provided on the side surface 110 of the partition layer 11 will be specifically described.

In the partition layer 11 of the microfluidic chip 1 according to the present embodiment, the curved surface 111 is formed on a part of the side surface 110 and curved in a convex shape in cross-sectional view. The "cross-section" in the "cross-sectional view" refers to a cross-section of the microfluidic chip 1 cut in the thickness direction (direction perpendicular to the longitudinal direction of the fluidic channel portion 13), for example, and the cross-section includes at least the partition layer 11, the cover layer 12 and the fluidic channel portion 13. In other words, the curved surface 111 includes the edge 101*a*, which is the edge on the fluidic channel portion 13 side of the upper contact surface 101 of the partition layer 11 (contact surface in contact with the first support member), and the curved surface 111 is curved away from the cover layer 12 at the edge 101*a* of the upper contact surface 101 (starting from the edge 101*a*).

As described above, the curved surface 111 of the partition layer 11 extends from the intermediate end 110*a*, which corresponds to the upper end of the flat surface 112, to the edge 101*a*. The curved surface 111 includes the edge 101*a*, which is one end (in this example, upper end) of the side surface 110, and is connected to the cover layer 12 at the edge 101*a*.

The curved surface 111 is provided on the side surface 110 of the upper region 11*a* of the partition layer 11, that is, on a region of the side surface 110 on the cover layer 12 side.

As shown in FIG. 2, in the upper region 11*a* of the partition layer 11, the edge 101*a*, which is the upper end of the curved surface 111 (edge on the fluidic channel portion 13 side of the upper contact surface 101), is located further away from the center of the fluidic channel portion 13 than the lower end of the curved surface 111 (intermediate end 110*a*) is. That is, the upper end of the curved surface 111 (edge 101*a*) is located further away from the opposing partition layer 11 than the intermediate end 110*a* is.

In other words, in the partition layer 11, the lower end of the curved surface 111 (intermediate end 110*a*) is located closer to the center of the fluidic channel portion 13 than the upper end of the curved surface 111 (edge 101*a*) is. That is, the lower end of the curved surface 111 (intermediate end 110*a*) is located closer to the opposing partition layer 11 than the upper end of the curved surface 111 (edge 101*a*) is.

The curved surface 111 is curved in a convex shape from the intermediate end 110*a* connected to the flat surface 112 to the upper end of the side surface 110 (edge 101*a*), where it is connected to the cover layer 12. Specifically, the curved surface 111 is curved, starting from the intermediate end 110*a*, away from the center of the fluidic channel portion 13 and the opposing partition layer 11, and connected to the cover layer 12.

Thus, the width W1 of the partition layer 11 in cross-sectional view decreases in the direction away from the center of the fluidic channel portion 13 and the opposing partition layer 11, as it approaches the cover layer 12. Therefore, the width W1 of the partition layer 11 in cross-sectional view decreases toward the cover layer 12.

The width W1 of the partition layer 11 continuously decreases toward the cover layer 12. More specifically, the width W1 of the upper region 11*a* of the partition layer 11 continuously decreases in the direction away from the center of the fluidic channel portion 13 and the opposing partition layer 11, as it approaches the cover layer 12.

The "continuously decreases" herein means that the width W1 of the partition layer 11 continuously decreases, without increasing (expanding), from the intermediate end 110*a* where the curved surface 111 of the upper region 11*a* is connected to the flat surface 112 to the edge 101*a* where the curved surface 111 is connected to the cover layer 12.

As shown in FIG. 2, a convex portion 111*a*, which is the most protruding portion of the curved surface 111 curved in a convex shape, is located further away from the center of the fluidic channel portion 13 than the intermediate end 110*a*, which is the lower end of the curved surface 111 (upper end of the flat surface 112), is. Therefore, the width W1 of the partition layer 11 continuously decreases, without increasing, even in the convex portion 111*a* of the curved surface 111. With this configuration, the fluidic channel width W2 can be reliably increased on the cover layer 12 side of the fluidic channel portion 13, whereby the bubble trapping region 130 is provided between the cover layer 12 and the partition layer 11.

As shown in FIG. 2, the curved portion 115 is provided in the upper region 11*a* of the partition layer 11. The curved portion 115 includes the curved surface 111 at the edge on the fluidic channel portion 13 side. Accordingly, the curved portion 115 is curved away from the cover layer 12 at the edge 101*a* on the fluidic channel portion 13 side of the upper contact surface 101. With this configuration, the fluidic channel width W2 increases on the cover layer 12 side of the fluidic channel portion 13, whereby the bubble trapping region 130 is provided.

As shown in FIG. 2, in the upper region 11*a* of the partition layer 11, the edge 101*a* of the upper contact surface 101 (upper end of the side surface 110) and the intermediate end 110*a* of the side surface 110 are connected by the curved surface 111 having an arc shape which is convex in cross-sectional view. Accordingly, as shown in FIG. 2, the edge on the fluidic channel portion 13 side of the curved portion 115 has a rounded corner shape. Due to the edge on the fluidic channel portion 13 side of the curved portion 115 having the rounded corner shape, the stability of fluid flow in the fluidic channel portion 13 can be further improved. Further, air bubbles in the fluidic channel portion 13 are more likely to be collected in the bubble trapping region 130.

Next, the configuration of the fluidic channel portion 13 defined by the substrate 10, the partition layer 11 and the cover layer 12 will be described. The fluidic channel width W2 of the fluidic channel portion 13 is defined as the width between a pair of partition layers 11 facing each other, that is, the width between the side surfaces 110.

As described above, the width W1 of the partition layer 11 in cross-sectional view decreases toward the cover layer 12. Accordingly, as shown in FIG. 2, the width between the side surfaces 110 of the pair of partition layers 11 is wider on the cover layer 12 side than on the substrate 10 side. Therefore, the fluidic channel width W2 of the fluidic channel portion 13 increases from the substrate 10 side toward the cover layer 12 side.

Specifically, the fluidic channel width W2 is narrowest in a region of the lowest part (bottom) of the fluidic channel portion 13 where a front surface 10*a* of the substrate 10 is exposed, that is, between the edges 102*a* of the pair of partition layers 11. As described above, the width W1 of the partition layer 11 is constant in the lower region 11*b* which includes the flat surface 112 extending from the lower end of the side surface 110 (edge 102*a*) to the intermediate end 110*a*. Accordingly, the fluidic channel width W2 between the lower regions 11*b* of the pair of partition layers 11, that is, the fluidic channel width W2 between the flat surfaces 112 of the pair of partition layers 11, is constant. That is, the fluidic channel width W2 of the fluidic channel portion 13 is narrowest in the region between the flat surfaces 112.

Further, the fluidic channel width W2 is widest at the top of the fluidic channel portion 13 where the rear surface 12*a* of the cover layer 12 is exposed, that is, between the upper ends (edges 101*a*) of the side surfaces 110 of the pair of partition layers 11.

As described above, the width W1 of the partition layer 11 continuously decreases toward the cover layer 12 in the upper region 11*a* which includes the curved surface 111 extending from the intermediate end 110*a* of the side surface 110 to the edge 101*a*. Specifically, as shown in FIG. 2, in the opposing pair of partition layers 11, the curved portions 115 provided in the upper regions 11*a* are curved such that the edges on the fluidic channel portion 13 side (curved surfaces 111) are separated from each other. Further, the curved portion 115 is curved away from the cover layer 12 at the edge on the fluidic channel portion 13 side.

Accordingly, the fluidic channel width W2 between the upper regions 11*a* of the pair of partition layers 11, that is, the fluidic channel width W2 between the curved surfaces 111 of the pair of partition layers 11, continuously increases toward the cover layer 12. In other words, the fluidic channel width W2 increases in a direction away from the center of the fluidic channel portion 13, as it approaches the cover layer 12. That is, a region between the curved surfaces 111 in the fluidic channel portion 13 is a region in which the fluidic channel width W2 continuously increases (expands) toward the cover layer 12.

The "continuously increases (expands)" herein means that the fluidic channel width W2 of the fluidic channel portion 13 continuously increases (expands), without decreasing, from the intermediate portion of the fluidic channel portion 13 (between the intermediate ends 110*a* of the pair of partition layers 11) toward the top of the fluidic channel portion 13 (between the edges 101*a* of the pair of partition layers 11).

Thus, the width of the fluidic channel portion 13 increases toward the cover layer 12 in a region formed by the curved portion 115 of the partition layer 11, more specifically, a region formed by the curved surface 111, and is constant in a region formed by a portion of the partition layer 11 other than the curved portion 115 (curved surface 111), that is, formed by the flat surface 112. With this configuration, a region with the reduced width W1 of the partition layer 11 can be limited to the cover layer 12 side, that is, the upper region 11*a* of the partition layer 11. Accordingly, the microfluidic chip 1 can ensure the area of the bonding region for bonding the partition layer 11 and the substrate 10, while ensuring the width of the fluidic channel width W2 sufficient to form the bubble trapping region 130 in a region between the curved surfaces 111 of the pair of partition layers 11. Therefore, the microfluidic chip 1 can enhance adhesion between the partition layer 11 and the substrate 10, while separating air bubbles in a micro fluidic channel into a specific region (bubble trapping region 130) to improve the stability of fluid flow.

Bubble Trapping Region

In the microfluidic chip 1 according to the present embodiment, the fluidic channel portion 13 includes a bubble trapping region 130 that traps air bubbles in the fluidic channel portion 13. As shown in FIG. 2, the bubble trapping region 130 is formed by the curved portion 115 (specifically, curved surface 111) of the partition layer 11 and the rear surface 12*a* which is the surface of the cover layer 12 on the fluidic channel portion 13 side.

Air bubbles may be present in the fluidic channel portion 13, for example, due to entrainment of air bubbles during injection of a fluid such as a reaction solution into the microfluidic chip 1, boiling due to heating of the reaction solution, air entrainment due to non-uniform flow in the microfluidic channel, foaming from the reaction solution itself, or the like.

If such air bubbles drift in the fluidic channel portion 13, especially in a center region E1 of the fluidic channel portion 13, which is the region near the center, fluid flow may become unstable, or visibility of the liquid may be reduced when the interior of the fluidic channel portion 13 is observed through the cover layer 12 or the substrate 10. As an example, in FIG. 2, a region of the fluidic channel portion 13 other than the bubble trapping region 130 is illustrated as a center region E1. The center region E1 is not limited to the position shown in FIG. 2 and may be limited to a region closer to the center of the fluidic channel portion 23.

In the microfluidic chip 1 according to the present embodiment, in which the bubble trapping region 130 is provided in the fluidic channel portion 13, air bubbles can be retained in a specific region (region other than the center region E1) in the fluidic channel portion 13. With this configuration, fluid flow can be stabilized and visibility during observation of the interior of the fluidic channel portion 13 can be improved.

As shown in FIG. 2, in the microfluidic chip 1 according to the present embodiment, the bubble trapping region 130 is a recess formed by the curved portion 115 (curved surface 111) of the partition layer 11 and the rear surface 12*a* of the cover layer 12, and the upper end of the curved surface 111 (edge 101*a*) is the deepest portion. More specifically, the bubble trapping region 130 is a corner formed by the curved surface 111 of the partition layer 11 and the rear surface 12*a* of the cover layer 12 connected to each other at the edge 101*a*, which is the upper end of the curved surface 111.

That is, the bubble trapping region 130 is formed on each of the left and right sides on the top of the fluidic channel at which the fluidic channel width W2 of the fluidic channel portion 13 is widest. Therefore, by separating air bubbles into the bubble trapping region 130, the air bubbles can be retained in a region away from the center region E1 of the fluidic channel portion 13. With this configuration, the microfluidic chip 1 according to the present embodiment can further improve the stability of fluid flow and further improve the visibility during observation of the interior of the fluidic channel portion 13.

Air bubbles in the fluidic channel portion 13 migrate (upward) in the fluid (e.g., reaction solution) from the center region E1 toward the left and right sides of the fluidic channel portion 13 due to pressure or the like when the fluid flows and are collected in the bubble trapping regions 130. As shown in FIG. 2, in the bubble trapping region 130 formed as a corner in this example, the height decreases toward the edge 101*a*, which is the deepest portion.

Accordingly, air bubbles collected in the bubble trapping region 130 are likely to remain in the bubble trapping region 130 and are less likely to leave toward the center region E1 of the channel portion 13.

As shown in FIG. 2, the bubble trapping region 130 is a region formed inside the fluidic channel portion 13 by the partition layer 11 and the cover layer 12 and is not formed by attaching a separate member with an adhesive. With this configuration, the microfluidic chip 1 can improve stability of fluid flow and prevent elution of an adhesive component into a solution in the fluidic channel to suppress inhibition of reaction of the solution.

Thus, the microfluidic chip 1 according to the present embodiment includes the fluidic channel portion 13, the cover layer 12 which is the first support member, the substrate 10 which is the second support member, and a pair of partition layers 11 interposed between the cover layer 12 and the substrate 10 to define the fluidic channel portion 13. Further, the partition layer 11 has the curved portion 115 curved away from the cover layer 12 at the edge 101*a* on the fluidic channel portion 13 side of the upper contact surface 101 in contact with the cover layer 12. Furthermore, the fluidic channel portion 13 includes the bubble trapping region 130 formed by the curved portion 115 and the rear surface 12*a* which is a surface of the cover layer 12 on the fluidic channel portion 13 side, and the bubble trapping region 130 traps air bubbles in the fluidic channel portion 13.

With this configuration, the microfluidic chip 1 can separate air bubbles in a micro fluidic channel into a specific region to improve stability of fluid flow and prevent elution of an adhesive component into a solution in the fluidic channel to suppress inhibition of reaction of the solution.

Further, in the microfluidic chip 1, the fluidic channel width W2 of the fluidic channel portion 13 increases toward the cover layer 12 in a region formed by the curved portion 115 of the partition layer 11 and is constant in a region formed by a portion of the partition layer 11 other than the curved portion 115 (region formed by the flat surface 112). With this configuration, the microfluidic chip 1 can ensure the area of the bonding region for bonding the partition layer 11 and the substrate 10, stabilize fluid flow, and enhance adhesion between the partition layer 11 and the substrate 10.

Method of Producing Microfluidic Chip

Next, a method of producing a microfluidic chip 1 according to an embodiment of the present invention will be described. FIG. 2 is a flowchart showing an example method of producing a microfluidic chip 1 according to the present embodiment.

The following description will be given of a case where the partition layer 11 is made of a photosensitive resin.

S1

In a method of producing a microfluidic chip 1 according to the present embodiment, a process of applying a resin to the substrate 10 is first performed. Thus, a resin layer for forming the partition layer 11 is provided on the substrate 10. In a method of producing a microfluidic chip 1 according to the present embodiment, a resin layer (photosensitive resin layer) made of a photosensitive resin, for example, may be formed on the substrate 10.

The photosensitive resin layer may be formed on the substrate 10 by, for example, applying a photosensitive resin to the substrate 10. The application may be performed by, for example, spin coating, spray coating, bar coating, or the like, and in particular, spin coating is preferred from the perspective of controlling the film thickness. Various forms of photosensitive resin, such as liquid, gel and film, can be applied to the substrate 10. In particular, it is preferred to form a photosensitive resin layer using a liquid resist.

Further, the resin (for example, photosensitive resin) may be applied to the substrate 10 so that the thickness of the resin layer (for example, photosensitive resin layer), that is, thickness of the partition layer 11, becomes in the range of 5 μm or greater and 100 μm or less.

S2

After the photosensitive resin is formed on the substrate 10, a process of heat treatment (pre-bake treatment) is performed to remove the solvent contained in the resin (for example, photosensitive resin) applied to the substrate 10. In the method of producing a microfluidic chip 1 according to the present embodiment, the pre-bake treatment is not an essential process, and may be appropriately performed at an optimal temperature and time according to the characteristics of the resin. For example, when the resin layer on the substrate 10 is a photosensitive resin, the pre-bake temperature and time are appropriately set to optimal conditions according to the characteristics of the photosensitive resin.

S3

Next, a process of exposing the resin (for example, photosensitive resin) applied to the substrate 10 is performed. Specifically, exposure is performed to draw a fluidic channel pattern on the photosensitive resin applied to the substrate 10. Exposure may be performed with, for example, an exposure device using ultraviolet light as a light source or a laser drawing device. In particular, exposure with a proximity exposure device or a contact exposure device using ultraviolet light as a light source is preferred. When using a proximity exposure device, exposure is performed via a photomask having a fluidic channel pattern of the microfluidic chip 1. The photomask may be one having a light-shielding film with a bilayer structure of chromium and chromium oxide.

Further, as described above, the partition layer 11 is formed of a photosensitive resin that is photosensitive to light having a wavelength of 190 nm or greater and 400 nm or less, which is in the ultraviolet light region. Accordingly, in this process (exposure process), the photosensitive resin applied to the substrate 10 may be exposed to light having a wavelength of 190 nm or greater and 400 nm or less.

Further, when a chemically amplified resist or the like is used to form a resin layer on the substrate 10, heat treatment (post exposure bake: PEB) may be further performed after the exposure to promote catalytic reaction of the acid generated by exposure.

S4

Next, a process of subjecting the exposed photosensitive resin to development is performed to form a fluidic channel pattern.

Development may be performed by reaction between the photosensitive resin and a developer using, for example, a spray, dip or puddle type development device. Examples of the developer include a sodium carbonate aqueous solution, tetramethylammonium hydroxide, potassium hydroxide and organic solvents. The developer is not limited to those described above, and a developer most suitable for the characteristics of the photosensitive resin may be appropriately used. Further, the concentration and development treatment time may be appropriately adjusted to optimal conditions according to the characteristics of the photosensitive resin.

S5

Next, a process of cleaning is performed to completely remove the developer used for development from the resin layer (photosensitive resin layer) on the substrate 10. Cleaning may be performed using, for example, a spray, shower or immersion type cleaning device. Examples of the cleaning solution include pure water, isopropyl alcohol, and the like, and the cleaning solution most suitable for removing the developer used for the development treatment may be appropriately used. After cleaning, drying is performed using a spin dryer, IPA vapor dryer, or by natural drying, or the like.

S6

Next, a process of heat treatment (post-bake) is performed on the partition layer 11 constituting the fluidic channel pattern, that is, the fluidic channel portion 13. This post-bake treatment removes residual water from development and cleaning. The post-bake treatment may be performed using, for example, a hot plate, oven, or the like. When drying in the cleaning process of S5 is insufficient, the developer and water from cleaning may remain in the partition layer 11. Further, the solvent that has not been removed in the pre-bake treatment may also remain in the partition layer 11. These can be removed by the post-bake treatment.

S7

Next, a process of bonding is performed to bond the cover layer 12 to the partition layer 11 after the post-bake treatment. In this process, as shown in FIG. 2), the cover layer 12 is bonded to a side of the partition layer 11 opposite to that facing the substrate 10. Thus, the fluidic channel portion 13 is covered with the cover layer 12, and the microfluidic chip 1 shown in FIG. 1 and FIG. 2 is formed.

The method of bonding the partition layer 11 and the cover layer 12 may be a method by thermocompression bonding after applying a surface modification treatment to the bonding surfaces of the partition layer 11 and the cover layer 12, a method using an adhesive, or a method of bonding by applying a surface modification treatment to the bonding surfaces of the partition layer 11 and the cover layer 12.

For example, in the method by thermocompression bonding described above, a surface modification treatment may be applied, after the post-bake treatment, to the partition layer 11 and the cover layer 12 (lid material) before being bonded to the partition layer 11. The surface modification treatment may be, for example, plasma treatment.

When the substrates subjected to surface modification treatment are bonded to each other by thermocompression bonding, thermocompression bonding using a heat press machine or a heat roll machine is preferred. It is preferred to form holes corresponding to the inlet 4 and the outlet 5 (see FIG. 1) for a fluid in advance in the cover layer 12 before it is bonded to the partition layer 11. This can prevent problems of dust and contamination from occurring compared with the case where holes are formed in the cover layer 12 after it is bonded to the partition layer 11.

Further, when the partition layer 11 and the cover layer 12 are bonded using an adhesive, the adhesive can be determined according to affinity with the materials constituting the partition layer 11 and the cover layer 12. The adhesive is not specifically limited as long as it can bond the partition layer 11 and the cover layer 12 together. Examples of the adhesive according to the present embodiment include acrylic resin adhesives, urethane resin adhesives and epoxy resin adhesives.

Further, the method of bonding by surface modification treatment may be plasma treatment, corona discharge treatment, excimer laser treatment, or the like. In this case, while improving the reactivity of the surface of the partition layer 11, an optimal treatment method may be appropriately selected according to the affinity and adhesion between the partition layer 11 and the cover layer 12.

Thus, in the method of producing a microfluidic chip 1 according to the present embodiment, the partition layer 11 defining the fluidic channel portion 13 can be formed on the substrate 10 using photolithography.

For example, when the photosensitive resin applied to the substrate 10 is a positive resist, the photosensitive resin in the exposed region dissolves during development and becomes the fluidic channel portion 13, and the photosensitive resin remaining in the unexposed region becomes the partition layer 11. Further, when the photosensitive resin applied to the substrate 10 is a negative resist, the photosensitive resin remaining in the exposed region becomes the partition layer 11, and the photosensitive resin in the unexposed region dissolves during development and becomes the fluidic channel portion 13.

In the present embodiment, by removing excess resin (in this example, photosensitive resin) on the substrate 10 in the development process (S4), the partition layer 11 can be formed to have the width W1 which decreases toward the cover layer 12 in cross-sectional view.

In the present embodiment, the shape of the partition layer 11 can be controlled by adjusting, for example, the development time and the concentration of the developer in development. As an example, the longer the development time, the more resin can be dissolved. Specifically, for example, by increasing the development time, more resin can be dissolved in the upper part of the photosensitive resin layer (on the side to which the cover layer 12 is bonded) than in the lower part (on the substrate 10 side). In this case, the amount of resin remaining on the side of the partition layer 11 where the upper region 11*a* is formed can be smaller than the amount of resin remaining on the side where the lower region 11*b* is formed. Accordingly, the partition layer 11 can be formed to have the width W1 which decreases toward the cover layer 12 (width W1 decreasing toward the cover layer 12 in cross-sectional view).

Further, the shape of the side surface 110 of the partition layer 11 can be formed in a desired shape by adjusting, for example, the development time and the amount of developer used in development.

Specifically, the curved portion (an example of the upper curved portion) 115 curved in a convex shape at the edge 101*a* on the fluidic channel portion 13 side of the upper contact surface 101 of the partition layer 11 (surface opposite to that facing the substrate 10) can be formed by development. For example, when forming the upper region 11*a* of the partition layer 11 in development, by dissolving and removing more resin especially on the fluidic channel portion 13 side, the curved portion 115 having the curved surface 111 curved in a concave shape can be formed.

Further, when forming the lower region 11*b* of the partition layer 11 in development, a constant amount of resin may be dissolved and removed in a partial region from the lower side (side connected to the substrate 10) of the photosensitive resin layer so that a constant amount of resin remains. Accordingly, the width W1 of the partition layer 11 in the lower region 11*b* of the partition layer 11 can be constant. Further, by adjusting the development time, the concentration of the developer, and the like, the side surface 110 of the lower region 11*b* can be formed in a planar shape as the flat surface 112.

Thus, in the method of producing a microfluidic chip 1, the curved portion 115 and the flat surface 112 can be formed on the side surface 110 of the partition layer 11 by controlling the degree of dissolution of the photosensitive resin layer by development.

When the photosensitive resin layer is formed of a positive resist, the closer to the upper part of the photosensitive resin layer (the closer to the connection to the cover layer 12), the higher the amount of exposure, and the closer to the lower part (the closer to the substrate 10), the lower the amount of exposure. Accordingly, the closer to the upper part of the photosensitive resin layer, the more resin is dissolved and removed during development, and the closer to the lower part, the more resin remains without being dissolved during development. Therefore, the photosensitive resin that remains on the substrate 10 to form the partition layer 11 increases toward the substrate 10. Thus, by using a positive resist, the amount of remaining resin can be more easily reduced toward the cover layer 12 in the upper region 11*a* of the partition layer 11. That is, the curved portion 115 can be more easily formed.

Further, by bonding the cover layer 12 to the partition layer 11 formed as described above (S7), the bubble trapping region 130 that traps air bubbles in a fluidic channel can be formed without attaching a separate member with an adhesive. Specifically, by bonding the cover layer 12 to the partition layer 11 having the curved portion 115, the bubble trapping region 130 can be formed between the curved portion 115 and the rear surface 12*a* of the cover layer 12 on the fluidic channel portion 13 side.

As described above, the method of producing a microfluidic chip 1 according to the present embodiment includes: applying a resin to a substrate 10 (the above S1); exposing the applied resin to light (the above S3); subjecting the exposed resin to development and cleaning to thereby form a partition layer 11 that defines a fluidic channel portion 13 on the substrate 10 (the above S4 and S5); post-baking the partition layer 11 (the above S6); and bonding a cover layer 12 to a side of the partition layer 11 opposite to that facing the substrate 10 (the above S7). Further, by removing excess resin (in this example, photosensitive resin) on the substrate 10 in the development process (S4), the upper curved portion (curved portion 115) curved in a convex shape at the edge on the fluidic channel portion 13 side of the upper contact surface 101 of the partition layer 11, which is a surface opposite to that facing the substrate 10, that is, the edge 101*a*, is formed.

With this configuration, in the microfluidic chip 1, a specific region (bubble trapping region 130) for trapping air bubbles can be formed between the curved portion 115 of the partition layer 11 and the cover layer 12 (specifically, the rear surface 12*a*). Therefore, the microfluidic chip 1 can separate air bubbles in a micro fluidic channel into the specific region to improve the stability of fluid flow. Further, as described above, the bubble trapping region 130 is not formed by attaching a separate member with an adhesive. Therefore, the microfluidic chip 1 can prevent elution of an adhesive component into a solution in the fluidic channel to suppress inhibition of reaction of the solution.

Thus, according to the production method described above, the microfluidic chip 1 can be obtained which can separate air bubbles in a micro fluidic channel into a specific region to improve stability of fluid flow and prevent elution of an adhesive component into a solution in the fluidic channel to suppress inhibition of reaction of the solution.

MODIFIED EXAMPLES

Figure 4:
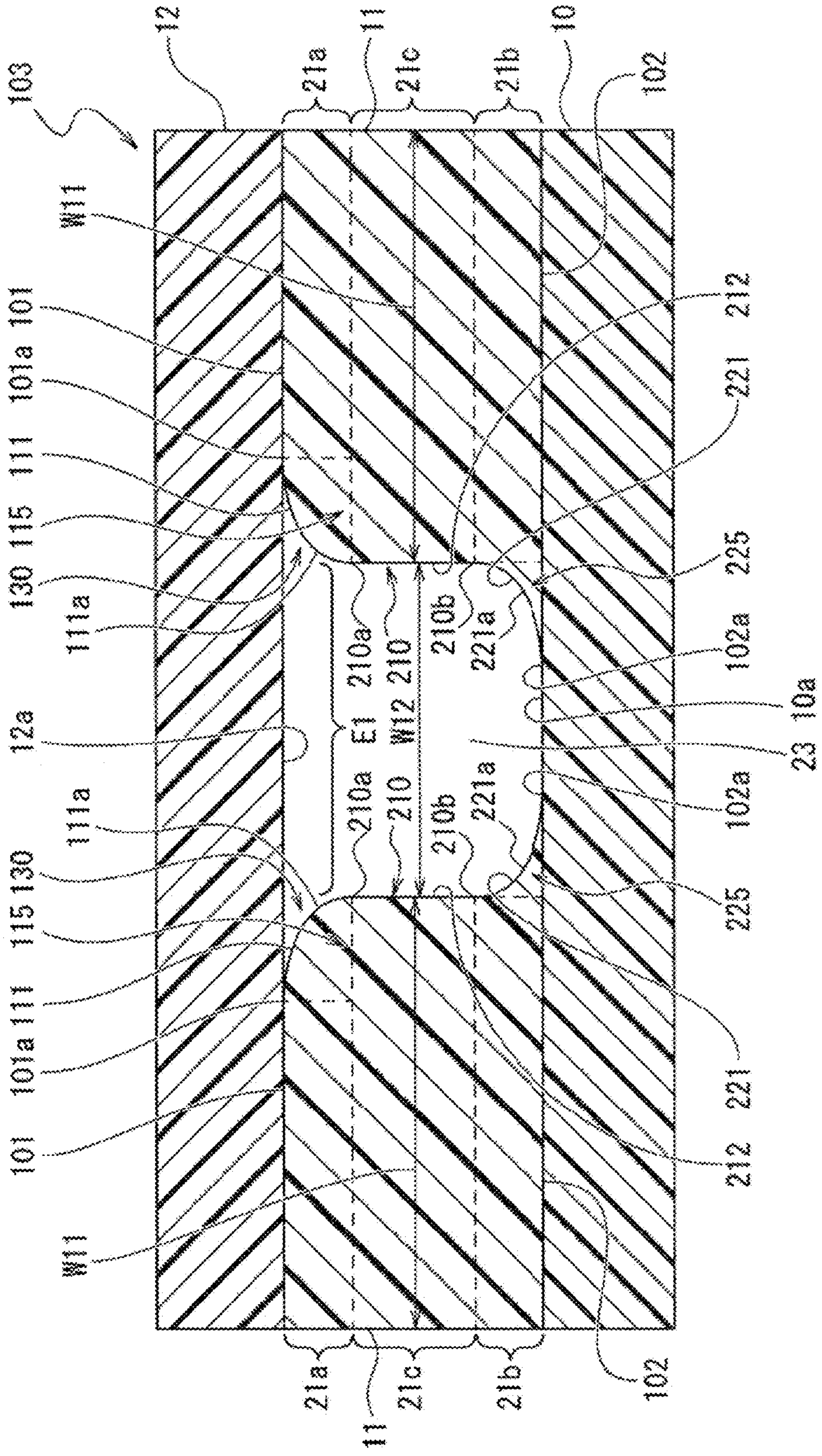
FIG. 4 is a schematic cross-sectional diagram illustrating an example configuration of a microfluidic chip according to a modified example of the first embodiment of the present invention.

With reference to FIG. 4, a microfluidic chip according to a modified example of the present embodiment will be described. FIG. 4 is a cross-sectional diagram illustrating an example configuration of a microfluidic chip 103 according to the modified example of the present embodiment.

The microfluidic chip 103 includes a substrate 10, a partition layer 21 that defines a fluidic channel portion 23 on the substrate 10, and a cover layer 12. As shown in FIG. 4, the microfluidic chip 103 differs from the microfluidic chip 1 described above in that a lower region 21*b* of the partition layer 21 has a flared shape of an extension portion 225.

The following description will be given of the partition layer 21 and the fluidic channel portion 23 defined by the partition layer 21. Components other than the partition layer 21 and the fluidic channel portion 23 (substrate 10 and cover layer 12) have the same configuration as the substrate 10 and the cover layer 12 of the microfluidic chip 1, so the same reference signs are used and the description thereof will be omitted.

Shape of Partition Layer and Configuration of Fluidic Channel

In the following description, details of the shape of the partition layer 21 and the configuration of the fluidic channel portion 23 in the microfluidic chip 103 according to this modified example will be described. First, the shape of the partition layer 21 that defines the fluidic channel portion 23 will be described.

As shown in FIG. 4, the partition layer 21 of the microfluidic chip 103 includes the upper contact surface 101, a lower contact surface 102 and a side surface 210. In the partition layer 21 of the microfluidic chip 103, the same configurations as the partition layer 11 of the microfluidic chip 1 are denoted by the same reference signs, and the description thereof will be omitted.

As shown in FIG. 4, the partition layer 21 of the microfluidic chip 103 has the extension portion 225 which extends in a transverse direction of the fluidic channel portion 23 along the front surface 10*a* of the substrate 10 which is the second support member, the partition layer 21 having a width increasing toward the second support member in cross-sectional view. With this configuration, in the microfluidic chip 103, the area of the bonding region for bonding the partition layer 21 and the substrate 10 increases. That is, the partition layer 21 has a shape in which a width W11 decreases toward the cover layer 12 which is the first support member in cross-sectional view and increases toward the substrate 10 which is the second support member.

With this configuration, the microfluidic chip 103 can improve stability of fluid flow, prevent elution of an adhesive component into a solution in the fluidic channel to suppress inhibition of reaction of the solution, and enhance adhesion between the partition layer 21 and the substrate 10.

The "cross-section" in the "cross-sectional view" refers to a cross-section of the microfluidic chip 103 cut in the thickness direction (direction perpendicular to the longitudinal direction of the fluidic channel portion 23), for example, and the cross-section includes the substrate 10, the partition layer 21, the cover layer 12 and the fluidic channel portion 23. In the following description, the shape of the partition layer 21 will be more specifically described.

The side surface 210 is the side surface of the partition layer 21, and a surface defining the fluidic channel portion 23. In this modified example, the edge 101*a* corresponds to the upper end of the side surface 210, and the edge 102*a* corresponds to the lower end of the side surface 210.

As shown in FIG. 4, the curved surface 111 is provided on one end side of the side surface 210. Specifically, as with the microfluidic chip 1, the curved surface 111 is provided on the upper end (edge 101*a*) side of the side surface 210.

Further, a curved surface 221 which is an inclined surface curved in a concave shape is provided on the other end side of the side surface 210. Specifically, the curved surface 221 is provided on the lower end (edge 102*a*) side of the side surface 210. Further, a flat surface 212 is formed in a region of the side surface 210 in which the curved surfaces (curved surfaces 111 and 221) are not provided, that is, a region between the curved surface 111 and the curved surface 221. The partition layer 21 of the microfluidic chip 103 differs from the partition layer 11 of the microfluidic chip 1 in that the side surface 210 of the partition layer 21 has the curved surface 111 and the curved surface 221 at respective ends.

The flat surface 212 is connected to the curved surface 111 at a first intermediate end 210*a* and connected to the curved surface 221 at a second intermediate end 210*b*. That is, the flat surface 212 extends from the first intermediate end 210*a* to the second intermediate end 210*b* of the side surface 210, with the first intermediate end 210*a* corresponding to the upper end of the flat surface 212 and the second intermediate end 210*b* corresponding to the lower end of the flat surface 212.

Further, the curved surface 111 is connected to the flat surface 212 at the first intermediate end 210*a* of the partition layer 21, instead of the intermediate end 110*a* of the partition layer 11 in the microfluidic chip 1. That is, in this modified example, the curved surface 111 extends from the edge 101*a*, which is the upper end of the side surface (in this example, side surface 210) to the first intermediate end 210*a*, and the first intermediate end 210*a* of the side surface 210 corresponds to the lower end of the curved surface 111. The other configurations of the curved surface 111 of the microfluidic chip 103 according to this modified example are the same as the curved surface 111 of the microfluidic chip 1. Similarly, the curved portion 115 having the curved surface 111 of the microfluidic chip 103 according to this modified example is the same as the curved portion 115 of the microfluidic chip 1.

Detailed description of the curved surface 111 and the curved portion 115 of this modified example will be omitted.

Further, the curved surface 221 is connected to the flat surface 212 at the second intermediate end 210*b* of the side surface 210 and connected to the substrate 10 at the edge 102*a*, which is the lower end of the side surface 210. That is, the curved surface 221 extends from the second intermediate end 210*b* to the edge 102*a* of the side surface 210, with the second intermediate end 210*b* of the side surface 210 corresponding to the upper end of the curved surface 221 and the edge 102*a*, which is the lower end of the side surface 210 corresponding to the lower end of the inclined surface 221.

Hereinafter, a region of the partition layer 21 including the curved surface 111 is referred to as an upper region 21*a*, a region including the curved surface 221 is referred to as a lower region 21*b*, and a region including the flat surface 212 is referred to as an intermediate region 21*c*. In FIG. 4, the upper region 21*a*, the lower region 21*b* and the intermediate region 21*c* of the partition layer 21 are divided by a virtual dotted line for ease of understanding. In the partition layer 21, the upper region 21*a*, the lower region 21*b* and the intermediate region 21*c* are preferably formed integrally but may be formed separately. That is, the partition layer 21 may have a multilayer (e.g., three-layer) structure.

The width W11 of the partition layer 21 decreases toward the cover layer 12 in the upper region 21*a* which includes the curved surface 111, increases toward the substrate 10 in the lower region 21*b* which includes the curved surface 221, and is constant in the intermediate region 21*c* which includes the flat surface 212. With this configuration, the microfluidic chip 103 can ensure a region for forming the bubble trapping region 130 in the fluidic channel portion 23 and increase the area of the bonding region for bonding the partition layer 21 and the substrate 10, while maintaining the width (fluidic channel width W12) of the fluidic channel portion 23 defined by the partition layer 21.

Next, the curved surface 221 provided on the side surface 210 of the partition layer 21 will be specifically described. The curved surface 221 is formed on a part of the remaining side surface 210 (side surface 210 of the lower region 21*b* of the partition layer 21) and curved in a concave shape in cross-sectional view. That is, the curved surface 221 is provided on a region of the side surface 210 on the substrate 10 side.

As shown in FIG. 4, in the lower region 21*b* of the partition layer 21, the edge 102*a*, which is the lower end of the side surface 210, is located closer to the center of the fluidic channel portion 23 than the upper end of the curved surface 221 (second intermediate end 210*b*) is. Specifically, the lower contact surface 102 of the partition layer 21 extends in the direction toward the center of the fluidic channel portion 23 (direction toward the opposing partition layer 21) along the front surface 10*a* of the substrate 10. Accordingly, the lower end of the side surface 210 (edge 102*a*) is located closer to the opposing partition layer 21 than the second intermediate end 210*b* is.

In other words, in the partition layer 21, the upper end of the curved surface 221 (second intermediate end 210*b*) is located further away from the center of the fluidic channel portion 23 than the lower end of the curved surface 221 (edge 102*a*) is. That is, the upper end of the curved surface 221 (second intermediate end 210*b*) is located further away from the opposing partition layer 21 than the edge 102*a*, which is the lower end of the curved surface 221, is.

The curved surface 221 is curved in a concave shape from the second intermediate end 210*b* to the edge 102*a*, where it is connected to the substrate 10. Thus, the width W11 of the partition layer 21 increases in the direction toward the center of the fluidic channel portion 23, that is, toward the opposing partition layer 21 (in the transverse direction of the fluidic channel portion 23), as it approaches the substrate 10. Therefore, the width W11 of the partition layer 21 in cross-sectional view increases toward the substrate 10.

The width W11 of the lower region 21*b* of the partition layer 21 continuously increases toward the substrate 10. More specifically, the width W11 of the lower region 21*b* of the partition layer 21 continuously expands and increases toward the center of the fluidic channel portion 23, that is, in the transverse direction, as it approaches the substrate 10. The "continuously increases (expands)" herein means that the width W11 of the partition layer 21 continuously increases (expands), without decreasing (reducing), from the second intermediate end 210*b*, which is the upper end of the curved surface 221, to the edge 102*a*, which is the lower end of the curved surface 221.

As shown in FIG. 4, in the curved surface 221 curved in a concave shape, a deepest portion 221*a* is located closer to the center of the fluidic channel portion 23 than the second intermediate end 210*b*, which is the upper end of the curved surface 221, is. Therefore, the width W11 of the partition layer 21 continuously increases, without decreasing, even in the deepest portion 211*a* of the curved surface 221. With this configuration, in the microfluidic chip 103, the area of the bonding region for bonding the partition layer 21 and the substrate 10 can be reliably increased, further reliably enhancing adhesion between the partition layer 21 and the substrate 10.

As shown in FIG. 4, the partition layer 21 has the extension portion 225 which extends in a transverse direction of the fluidic channel portion 23 along the front surface 10*a* of the substrate 10, the partition layer 21 having a width increasing toward the substrate 10 which is the second support member in cross-sectional view. Specifically, the extension portion 225 extends in the direction toward the center of the fluidic channel portion 23, that is, toward the opposing partition layer 21. Accordingly, the extension portion 225 has a flared shape, and the width of the partition layer 21 increases toward the substrate 10.

The extension portion 225 has the curved surface 221 curved in a concave shape in cross-sectional view. Accordingly, the extension portion 225 has a shape in which the thickness decreases in the transverse direction of the fluidic channel portion 23. With this configuration, compared with the case where the curved surface 221 has a planar shape, the microfluidic chip 103 can reduce a decrease in the width (fluidic channel width W12) of the fluidic channel portion 23 due to an increase in the width W11 of the partition layer 21, while increasing the area of the bonding region for bonding the partition layer 21 and the substrate 10.

As described above, in the microfluidic chip 103 according to this modified example, the partition layer 21 has the extension portion 225 which extends in a transverse direction of the fluidic channel portion 23 along the front surface 10*a* of the second support member (substrate 10), the partition layer 21 having a width increasing toward the second support member in cross-sectional view.

With this configuration, the microfluidic chip 103 can improve stability of fluid flow, prevent elution of an adhesive component into a solution in the fluidic channel to suppress inhibition of reaction of the solution, and enhance adhesion between the partition layer 21 and the substrate 10.

In the partition layer 21, the extension portion 225 has the curved surface 221 curved in a concave shape in cross-sectional view.

With this configuration, the microfluidic chip 103 can reduce a decrease in the width (fluidic channel width W12) of the fluidic channel portion 23 due to an increase in the width W11 of the partition layer 21, further improve stability of fluid flow, and enhance adhesion between the partition layer 21 and the substrate 10.

Next, the configuration of the fluidic channel portion 23 defined by the substrate 10, the partition layer 21 and the cover layer 12 will be described. The fluidic channel width W12 of the fluidic channel portion 23 is defined as the width between a pair of partition layers 21 facing each other, that is, the width between the side surfaces 210.

As described above, the width W11 of the partition layer 21 in cross-sectional view decreases toward the cover layer 12 and increases toward the substrate 10. Accordingly, as shown in FIG. 4, the width between the side surfaces 210 of the pair of partition layers 21 is wider on the cover layer 12 side than between the flat surfaces 212 and narrower on the substrate 10 side than between the flat surfaces 212. Therefore, the fluidic channel width W12 of the fluidic channel portion 23 increases toward the cover layer 12 and decreases toward the substrate 10 from the center region in the height of the fluidic channel portion 23 (thickness of the partition layer 21).

Specifically, the fluidic channel width W12 is widest at the top of the fluidic channel portion 23 where the rear surface 12*a* of the cover layer 12 is exposed, that is, between the upper ends of the side surfaces 210 (edges 101*a* of the upper contact surfaces 101) of the pair of partition layers 21. This is similar to the structure of the microfluidic chip 1 described above, in which the fluidic channel width W2 is widest at the top of the fluidic channel portion 13 (between the edges 101*a* of the pair of partition layers 11).

Further, the fluidic channel width W12 is narrowest at the bottom of the fluidic channel portion 23 where the front surface 10*a* of the substrate 10 is exposed, that is, between the lower ends (edges 102*a*) of the side surfaces 210 of the pair of partition layers 21.

As described above, the width W11 of the partition layer 21 continuously increases toward the substrate 10 in the lower region 21*b* which includes the curved surface 221 extending from the second intermediate end 210*b* to the lower end (edge 102*a*) of the side surface 210. Specifically, in the pair of partition layers 21 facing each other, each of the extension portions 225, which include the curved surface 221, approaches the other in the transverse direction of the fluidic channel portion 23.

Accordingly, the width between the extension portions 225 of the pair of partition layers 21 becomes narrower (decreases) toward the substrate 10. That is, the width of the fluidic channel portion 23 (fluidic channel width W12) decreases toward the substrate 10 in a region formed by the extension portion 225 of the partition layer 21. More specifically, the width between the curved surfaces 221 of the pair of partition layers 21 becomes continuously narrower (decreases) toward the substrate 10. That is, the fluidic channel width W12 between the curved surfaces 221 of the pair of partition layers 21 becomes continuously narrower (decreases) toward the substrate 10.

The "continuously decreases" herein means that the fluidic channel width W12 of the fluidic channel portion 23 continuously decreases, without increasing, from a region between the lower ends of the flat surfaces 212 (region between the second intermediate ends 210*b* of the pair of partition layers 21) toward the bottom of the fluidic channel portion 23 (between the edges 102*a* of the pair of partition layers 21).

As described above, the width W11 of the partition layer 21 is constant in the intermediate region 21*c* which includes the flat surface 212 extending from the first intermediate end 210*a* to the second intermediate end 210*b* of the side surface 210. Accordingly, the width between the flat surfaces 212 in the pair of partition layers 21 is constant. That is, the fluidic channel width W12 between the flat surfaces 212 (between the intermediate regions 21*c*) of the pair of partition layers 21 is constant. More specifically, the fluidic channel width W12 between the flat surfaces 212 is narrower than between the curved surfaces 111 (between the upper regions 21*a*) and wider than between the curved surfaces 221 (between the lower regions 21*b*).

Thus, the width of the fluidic channel portion 23 increases toward the cover layer 12 in a region formed by the curved portion 115 of the partition layer 21, more specifically, a region formed by the curved surface 111, and is constant in a region formed by the flat surface 212 of the partition layer 21.

Further, the width of the fluidic channel portion 23 (fluidic channel width W12) decreases toward the substrate 10 in a region formed by the extension portion 225 of the partition layer 21.

With this configuration, a region with the reduced width W11 of the partition layer 21 can be limited to the cover layer 12 side, that is, the upper region 21*a* of the partition layer 21, and the width W11 of the partition layer 21 can be increased in the lower region 21*b* of the partition layer 21. Accordingly, the microfluidic chip 103 can increase the area of the bonding region for bonding the partition layer 21 and the substrate 10, while ensuring the width of the fluidic channel width W12 sufficient to form the bubble trapping region 130 in a region between the curved surfaces 111 of the pair of partition layers 21. Therefore, the microfluidic chip 103 can enhance adhesion between the partition layer 21 and the substrate 10, while separating air bubbles in a micro fluidic channel into a specific region (bubble trapping region 130) to improve the stability of fluid flow.

Further, the fluidic channel width W12 is constant in a region formed by the flat surface 212 and is wider than a region formed by the extension portion 225. With this configuration, a region with the reduced fluidic channel width W12 can be limited to a region on the bottom side (substrate 10 side) of the fluidic channel portion 23, that is, between the curved surfaces 221. Accordingly, in the microfluidic chip 103, the area of the bonding region for bonding the partition layer 21 and the substrate 10 can be reliably increased, while maintaining the width of the fluidic channel width W12 of the fluidic channel portion 23 in a region between the flat surfaces 212 of the pair of partition layers 21. Therefore, the microfluidic chip 103 can reliably enhance adhesion between the partition layer 21 and the substrate 10, while improving flow stability of a fluid (e.g., reaction solution) in the fluidic channel portion 23 and visibility during observation of the interior of the fluidic channel portion 23.

Further, as shown in FIG. 4, the fluidic channel portion 23 has a rounded corner shape in cross-sectional view in a region between the lower regions 21*b* of the pair of partition layers 21, that is, a region between the curved surfaces 221. The "cross-section" in the "cross-sectional view" refers to a cross-section of the microfluidic chip 103 cut in the thickness direction (direction perpendicular to the longitudinal direction of the fluidic channel portion 23), and the cross-section includes the substrate 10, the partition layer 21, the cover layer 12 and the fluidic channel portion 23. Since the fluidic channel portion 23 has a rounded corner shape in cross-sectional view in a region between the curved surfaces 221, a fluid flow speed and a flow rate of a fluid (e.g., reaction solution) in the fluidic channel portion 23 can be stabilized.

In the microfluidic chip 103 according to this modified example, the fluidic channel portion 23 includes the bubble trapping region 130 that traps air bubbles in the fluidic channel portion 23. As shown in FIG. 4, the bubble trapping region 130 is formed by the curved portion 115 (specifically, curved surface 111) of the partition layer 21 and the rear surface 12*a* which is the surface of the cover layer 12 on the fluidic channel portion 23 side. The bubble trapping region 130 in the microfluidic chip 103 has the same configuration as the bubble trapping region 130 in the microfluidic chip 1, and detailed description thereof will be omitted.

Method of Producing Microfluidic Chip

Figure 3:
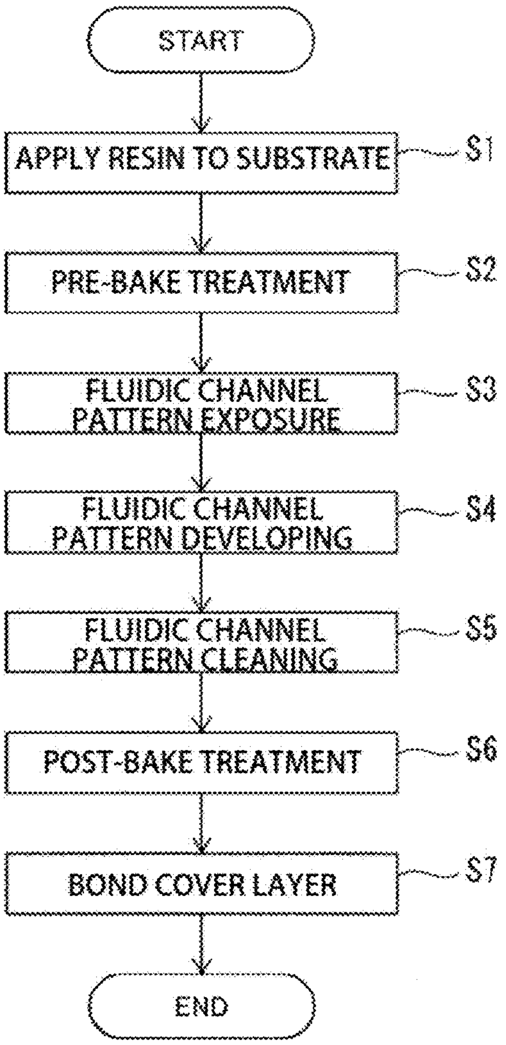
FIG. 3 is a flowchart showing an example method of producing a microfluidic chip according to the first embodiment of the present invention.

The basic method of producing a microfluidic chip 103 according to this modified example is the same as the method of producing a microfluidic chip 1 according to the first embodiment described above (see FIG. 3), and detailed description will be omitted. Also in this modified example, as with the microfluidic chip 1, the curved portion 115 and the flat surface (in this example, flat surface 212) may be formed by adjusting the development time, the amount of developer used, and the like in the development process (S4).

Further, in this modified example, by removing excess resin (in this example, photosensitive resin) on the substrate 10 in the development process (S4), the lower region 21*b* of the partition layer 21 can be formed in a flared shape. More specifically, by the development, the partition layer 21 can be formed in a shape in which the width increases toward the substrate 10 in cross-sectional view on the substrate 10 side of the partition layer 21. With this configuration, the microfluidic chip having further enhanced adhesion between the partition layer 21 and the substrate 10 can be obtained.

For example, in this modified example, in a region on the lower side the intermediate portion in the thickness direction of the photosensitive resin layer (in this example, the intermediate region 21*c* that forms the flat surface 212 in the partition layer 21), the degree of resin dissolution in the development may be reduced as it closer to the substrate 10. This reduces the amount of resin removed, so that more resin can remain as it closer to the substrate 10. Accordingly, the width W11 of the partition layer 21 in the lower region 21*b* of the partition layer 21 can be increased toward the substrate 10.

Further, by adjusting the development time, the concentration of the developer, and the like, the side surface 210 of the lower region 21*b* may be formed in a shape curved in a concave shape as the curved surface 221. Accordingly, the extension portion 225 including the curved surface 221 can be formed in the lower region 21*b*.

Thus, in the method of producing a microfluidic chip 103, the curved portion 115 and the flat surface 112 can be formed on the side surface 110 of the partition layer 11 by controlling the degree of dissolution of the photosensitive resin layer by development.

Second Embodiment

Configuration of Microfluidic Chip

Figure 5:
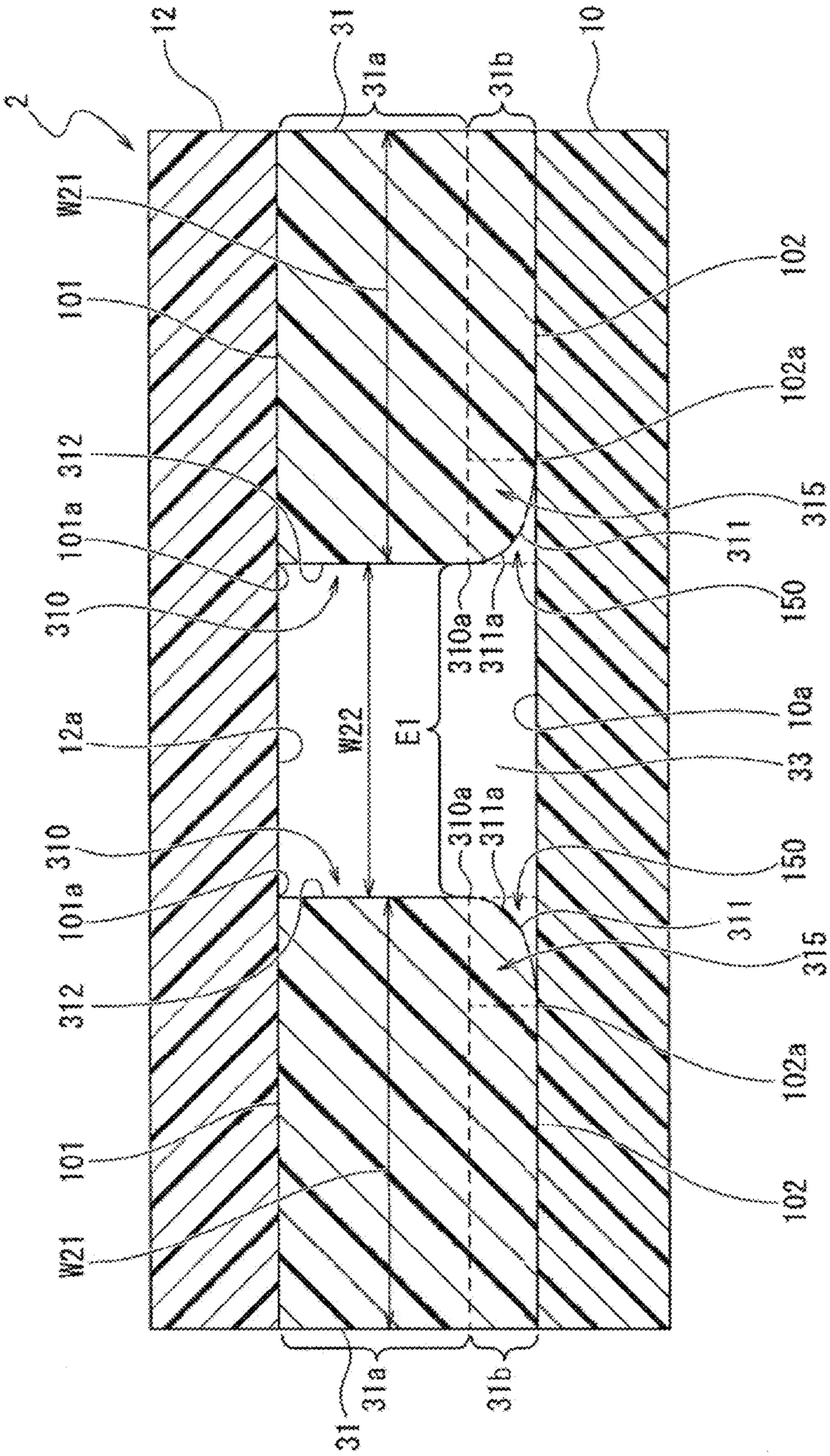
FIG. 5 is a schematic cross-sectional diagram illustrating an example configuration of a microfluidic chip according to a second embodiment of the present invention.

With reference to FIG. 5, a microfluidic chip according to a second embodiment of the present invention will be described. FIG. 5 is a cross-sectional diagram illustrating an example configuration of a microfluidic chip 2 according to the second embodiment of the present invention.

Overview of Microfluidic Chip

As shown in FIG. 5, the microfluidic chip 2 differs from the microfluidic chip 1 according to the first embodiment in that a curved portion 315 is provided on a lower region 31*b* of a partition layer 31. The following description will be given of the partition layer 31 and a fluidic channel portion 33 defined by the partition layer 31 in the microfluidic chip 2.

The substrate 10 and cover layer 12 in the microfluidic chip 2 have the same configuration as the substrate 10 and the cover layer 12 of the microfluidic chip 1, so the same reference signs are used and the description thereof will be omitted.

As shown in FIG. 5, in the microfluidic chip 2, the fluidic channel portion 33, which is a fluidic channel through which a fluid flows, is defined by walls sandwiched between two support members (first and second support members). In this example, the substrate 10 provided on the bottom side of the partition layer 31 to form the bottom of the fluidic channel portion 13 corresponds to the first support member, and the cover layer 12 provided on the upper side of the partition layer 31 to cover the upper part of the fluidic channel portion 13 corresponds to the second support member. That is, the microfluidic chip 2 includes the fluidic channel portion 33, the substrate (an example of first support member) 10, the cover layer (an example of second support member) 12, and a pair of partition layers (an example of partition member) 31 interposed between the substrate 10 and the cover layer 12 to define the fluidic channel portion 33. With this configuration, as with the microfluidic chip 1 described above, the microfluidic chip 2 can separate air bubbles in the fluidic channel portion 33 into a specific region to improve stability of fluid flow and prevent elution of an adhesive component into a solution in the fluidic channel to suppress inhibition of reaction of the solution.

Shape of Partition Layer and Configuration of Fluidic Channel

In the following description, details of the shape of the partition layer 31 and the configuration of the fluidic channel portion 33 in the microfluidic chip 2 according to the present embodiment will be described. First, the shape of the partition layer 31 that defines the fluidic channel portion 33 will be described. As shown in FIG. 5, the partition layer 31 of the microfluidic chip 2 includes the curved portion 315 on the substrate 10 side. That is, the partition layer 31 has a shape of the partition layer 11 of the microfluidic chip 1 according to the first embodiment inverted upside down.

Specifically, the partition layer 31 of the microfluidic chip 2 has the curved portion 315 curved away from the first support member (substrate 10) at the edge 102*a* on the fluidic channel side of the lower contact surface 102 in contact with the substrate 10, which is the first support member. Further, the fluidic channel portion 33 includes a bubble trapping region 150 formed by the partition layer 31 (specifically, the curved portion 315) and a surface of the first support member (substrate 10) on the fluidic channel portion 33 side (front surface 10*a*), and the bubble trapping region 150 traps air bubbles in the fluidic channel portion 33. With this configuration, the microfluidic chip 2 can separate air bubbles in the fluidic channel portion 33 into a specific region to improve stability of fluid flow. Further, the bubble trapping region 150 is not provided by attaching a separate member with an adhesive but is provided by forming the partition layer 31 into a specific shape (by forming the curved portion 315). With this configuration, the microfluidic chip 2 can prevent elution of an adhesive component into a solution in the fluidic channel to suppress inhibition of reaction of the solution. In the following description, the shape of the partition layer 31 will be more specifically described.

As shown in FIG. 5, the partition layer 31 of the microfluidic chip 2 includes the upper contact surface 101, the lower contact surface 102 and the side surface 110. In the partition layer 31 of the microfluidic chip 2, the same configurations as the partition layer 11 of the microfluidic chip 1 according to the first embodiment are denoted by the same reference signs, and the description thereof will be omitted.

The side surface 310 is the side surface of the partition layer 31, and a surface defining the fluidic channel portion 33. The side surface 310 extends from the edge 101*a* of the upper contact surface 101 of the partition layer 31 to the edge 102*a* of the lower contact surface and is connected to the cover layer 12 at the edge 101*a* (upper end of the side surface 310) and to the substrate 10 at the edge 102*a* (lower end of the side surface 310).

A curved surface 311 which is a curved inclined surface is provided on one end side of the side surface 310 (in this example, the edge 102*a* side on the substrate 10 side).

On the other hand, no curved surface is provided on the other end side, which is the upper end (edge 101*a*) side of the side surface 310. That is, in the side surface 310, the curved surface 311 does not include the upper end (edge 101*a*). In the side surface 310, a flat surface 312 is provided in a region where the curved surface 311 is not provided.

The flat surface 312 is connected to the cover layer 12 at the edge 101*a* (upper end of the side surface 310) of the partition layer 31 and connected to the curved surface 311 at an intermediate end 310*a* located between the edge 101*a* and the edge 102*a* of the partition layer 31. That is, the upper end (edge 101*a*) of the side surface 310 corresponds to the upper end of the flat surface 312, and the intermediate end 310*a* corresponds to the lower end of the flat surface 312.

Hereinafter, a region of the partition layer 31 including the flat surface 312 is referred to as an upper region 31*a*, and a region including the curved surface 311 (region including the curved portion 315 having the curved surface 311) is referred to as a lower region 31*b*. In FIG. 5, the upper region 31*a* and the lower region 31*b* of the partition layer 31 are divided by a virtual dotted line for ease of understanding. In the partition layer 31, the upper region 31*a* and the lower region 31*b* are preferably formed integrally but may be formed separately. That is, the partition layer 31 may have a multilayer (e.g., two-layer) structure.

The partition layer 31 has a width W21 which is constant throughout the upper region 31*a* including the flat surface 312 and decreases toward the substrate 10 in the lower region 31*b* including the curved surface 311. Accordingly, the area of the lower contact surface 102 in the partition layer 31 is smaller than the area of the upper contact surface 101. That is, the area of the bonding region for bonding the partition layer 31 and the substrate 10 is smaller than the area of the bonding region for bonding the partition layer 31 and the cover layer 12.

Therefore, in the microfluidic chip 2, the width of the fluidic channel portion 33 (fluidic channel width W22) increases toward the substrate 10, which is the first support member, in a region formed by the curved portion 315 having the curved surface 311 in the partition layer 31. Further, the fluidic channel width W22 is constant in a region formed by a portion other than the curved surface 311 of the partition layer 31 (in this example, flat surface 312). With this configuration, the microfluidic chip 2 can ensure a region for forming the bubble trapping region 150 in the fluidic channel portion 33. Details of the fluidic channel width W22 of the fluidic channel portion 33 and the bubble trapping region 150 will be described later.

In the present embodiment, although the area of the lower contact surface 102 of the partition layer 11 is smaller than the area of the upper contact surface 101, it is sufficient to maintain adhesion between the partition layer 31 and the substrate 10 in bonding these together and prevent occurrence of liquid leakage, damage, and the like during use of the microfluidic chip 2.

Next, the curved surface 311 provided on the side surface 310 of the partition layer 31 will be specifically described.

In the partition layer 31 of the microfluidic chip 2 according to the present embodiment, the curved surface 311 is formed on a part of the side surface 310 and curved in a convex shape in cross-sectional view. The "cross-section" in the "cross-sectional view" refers to a cross-section of the microfluidic chip 2 cut in the thickness direction (direction perpendicular to the longitudinal direction of the fluidic channel portion 33), for example, and the cross-section includes at least the partition layer 31, the cover layer 12 and the fluidic channel portion 33. In other words, the curved surface 311 includes the edge 102*a*, which is the edge on the fluidic channel portion 33 side of the lower contact surface 102 of the partition layer 31 (contact surface in contact with the first support member), and the curved surface 311 is curved away from the substrate 10 at the edge 102*a* of the lower contact surface 102 (starting from the edge 102*a*).

The curved surface 311 of the partition layer 31 extends from the intermediate end 310*a*, which corresponds to the lower end of the flat surface 312, to the edge 102*a*, which corresponds to the lower end of the side surface 310. The intermediate end 310*a* corresponds to the upper end of the curved surface 311, and the edge 102*a* corresponds to the lower end of the curved surface 311. The curved surface 311 includes the edge 102*a*, which is one end (in this example, lower end) of the side surface 310, and is connected to the substrate 10 at the edge 102*a*.

The curved surface 311 is provided on the side surface 310 of the lower region 31*b* of the partition layer 31, that is, on a region of the side surface 310 on the substrate 10 side.

As shown in FIG. 5, in the lower region 31*b* of the partition layer 31, the edge 102*a*, which is the lower end of the curved surface 311 (edge on the fluidic channel portion 33 side of the lower contact surface 102), is located further away from the center of the fluidic channel portion 33 than the upper end of the curved surface 311 (intermediate end 310*a*) is. That is, the lower end of the curved surface 311 (edge 102*a*) is located further away from the opposing partition layer 31 than the intermediate end 310*a* is.

In other words, in the partition layer 31, the upper end of the curved surface 311 (intermediate end 310*a*) is located closer to the center of the fluidic channel portion 33 than the lower end of the curved surface 311 (edge 102*a*) is. That is, the upper end of the curved surface 311 (intermediate end 310*a*) is located closer to the opposing partition layer 31 than the lower end of the curved surface 311 (edge 102*a*) is.

The curved surface 311 is curved in a convex shape from the intermediate end 310*a* connected to the flat surface 312 to the lower end of the side surface 310 (edge 102*a*), where it is connected to the substrate 10. Specifically, the curved surface 311 is curved, starting from the intermediate end 310*a*, away from the center of the fluidic channel portion 33 and the opposing partition layer 31, and connected to the substrate 10.

Thus, the width W21 of the partition layer 31 in cross-sectional view decreases in the direction away from the center of the fluidic channel portion 33 and the opposing partition layer 31, as it approaches the substrate 10. Therefore, the width W21 of the partition layer 31 in cross-sectional view decreases toward the substrate 10.

The width W21 of the partition layer 31 continuously decreases toward the substrate 10. More specifically, the width W21 of the lower region 31*b* of the partition layer 31 continuously decreases in the direction away from the center of the fluidic channel portion 33 and the opposing partition layer 31, as it approaches the substrate 10.

The "continuously decreases" herein means that the width W21 of the partition layer 31 continuously decreases, without increasing (expanding), from the intermediate end 310*a* where the curved surface 311 of the lower region 31*b* is connected to the flat surface 312 to the edge 102*a* where the curved surface 311 is connected to the substrate 10.

As shown in FIG. 5, a convex portion 311*a*, which is the most protruding portion of the curved surface 311 curved in a convex shape, is located further away from the center of the fluidic channel portion 33 than the intermediate end 310*a*, which is the upper end of the curved surface 311 (lower end of the flat surface 312) is. Therefore, the width W21 of the partition layer 31 continuously decreases, without increasing, even in the convex portion 311*a* of the curved surface 311. With this configuration, the fluidic channel width W22 can be reliably increased on the substrate 10 side of the fluidic channel portion 33, whereby the bubble trapping region 150 is provided between the substrate 10 and the partition layer 31.

As shown in FIG. 5, the curved portion 315 is provided in the lower region 31*b* of the partition layer 31. The curved portion 315 includes the curved surface 311 at the edge on the fluidic channel portion 33 side. Accordingly, the curved portion 315 is curved away from the substrate 10 at the edge 102*a* on the fluidic channel portion 33 side of the contact surface (lower contact surface 102) in contact with the first support member. With this configuration, the fluidic channel width W22 increases on the substrate 10 side of the fluidic channel portion 33, whereby the bubble trapping region 150 is provided.

As shown in FIG. 5, in the lower region 31*b* of the partition layer 31, the edge 102*a* of the lower contact surface 102 (lower end of the side surface 310) and the intermediate end 310*a* of the side surface 310 are connected by the curved surface 311 having an arc shape which is convex in cross-sectional view. Accordingly, as shown in FIG. 5, the edge on the fluidic channel portion 33 side of the curved portion 315 has a rounded corner shape. Due to the edge on the fluidic channel portion 33 side of the curved portion 315 having the rounded corner shape, the stability of fluid flow in the fluidic channel portion 33 can be further improved. Further, air bubbles in the fluidic channel portion 33 are more likely to be collected in the bubble trapping region 150.

Next, the configuration of the fluidic channel portion 33 defined by the substrate 10, the partition layer 31 and the cover layer 12 will be described. The fluidic channel width W22 of the fluidic channel portion 33 is defined as the width between a pair of partition layers 31 facing each other, that is, the width between the side surfaces 310. As described above, the width W21 of the partition layer 31 in cross-sectional view decreases toward the substrate 10. Accordingly, as shown in FIG. 5, the width between the side surfaces 310 of the pair of partition layers 31 is wider on the substrate 10 side than on the cover layer 12 side. Therefore, the fluidic channel width W22 of the fluidic channel portion 33 increases from the cover layer 12 side toward the substrate 10 side.

Specifically, the fluidic channel width W22 is narrowest in a region at the top of the fluidic channel portion 33 where the rear surface 12*a* of the cover layer 12 is exposed, that is, between the edges 101*a* of the pair of partition layers 31. As described above, the width W21 of the partition layer 31 is constant in the upper region 31*a* which includes the flat surface 312 extending from the upper end (edge 101*a*) to the intermediate end 310*a* of the side surface 310. Accordingly, the fluidic channel width W22 between the upper regions 31*a* of the pair of partition layers 31, that is, the fluidic channel width W22 between the flat surfaces 312 of the pair of partition layers 31, is constant. That is, the fluidic channel width W22 of the fluidic channel portion 33 is narrowest in the region between the flat surfaces 312.

Further, the fluidic channel width W22 is widest at the lowest part (bottom) of the fluidic channel portion 33 where the front surface 10*a* of the substrate 10 is exposed, that is, between the lower ends (edges 102*a*) of the side surfaces 310 of the pair of partition layers 31.

As described above, the width W21 of the partition layer 31 continuously decreases toward the substrate 10 in the lower region 31*b* which includes the curved surface 311 extending from the intermediate end 310*a* of the side surface 310 to the edge 102*a*. Specifically, as shown in FIG. 5, in the opposing pair of partition layers 31, the curved portions 315 provided in the lower regions 31*b* are curved such that the edges on the fluidic channel portion 33 side (curved surfaces 311) are separated from each other. Further, the curved portion 315 is curved away from the substrate 10 at the edge on the fluidic channel portion 33 side.

Accordingly, the fluidic channel width W22 between the lower regions 31*b* of the pair of partition layers 31, that is, the fluidic channel width W22 between the curved surfaces 311 of the pair of partition layers 31, continuously increases toward the substrate 10. In other words, the fluidic channel width W22 increases in a direction away from the center of the fluidic channel portion 33, as it approaches the substrate 10. That is, a region between the curved surfaces 311 in the fluidic channel portion 33 is a region in which the fluidic channel width W22 continuously increases (expands) toward the substrate 10.

The "continuously increases (expands)" herein means that the fluidic channel width W22 of the fluidic channel portion 33 continuously increases (expands), without decreasing, from the intermediate portion of the fluidic channel portion 33 (between the intermediate ends 310*a* of the pair of partition layers 31) toward the bottom of the fluidic channel portion 33 (between the edges 102*a* of the pair of partition layers 31).

Thus, the width of the fluidic channel portion 33 increases toward the substrate 10 in a region formed by the curved portion 315 of the partition layer 31, more specifically, a region formed by the curved surface 311, and is constant in a region formed by a portion of the partition layer 31 other than the curved portion 315 (curved surface 311), that is, formed by the flat surface 312. With this configuration, a region with the reduced width W21 of the partition layer 31 can be limited to the substrate 10 side, that is, the lower region 31*b* of the partition layer 31. Accordingly, the microfluidic chip 2 can ensure the area of the bonding region for bonding the partition layer 31 and the cover layer 12, while ensuring the width of the fluidic channel width W22 sufficient to form the bubble trapping region 150 in a region between the curved surfaces 311 of the pair of partition layers 31. Therefore, the microfluidic chip 2 can enhance adhesion between the partition layer 31 and the cover layer 12, while separating air bubbles in a micro fluidic channel into a specific region (bubble trapping region 150) to improve the stability of fluid flow.

Bubble Trapping Region

In the microfluidic chip 2 according to the present embodiment, the fluidic channel portion 33 includes a bubble trapping region 150 that traps air bubbles in the fluidic channel portion 33. As shown in FIG. 5, the bubble trapping region 150 is formed by the curved portion 315 (specifically, curved surface 311) of the partition layer 31 and the front surface 10*a* which is the surface of the substrate 10 on the fluidic channel portion 33 side. In this respect, the bubble trapping region 150 differs from the bubble trapping region 130 of the microfluidic chip 1 according to the first embodiment.

In the microfluidic chip 2 according to the present embodiment, in which the bubble trapping region 150 is provided in the fluidic channel portion 33, air bubbles can be retained in a specific region (region other than the center region E1) in the fluidic channel portion 33. With this configuration, as with the microfluidic chip 1, the microfluidic chip 2 can stabilize fluid flow and improve visibility during observation of the interior of the fluidic channel portion 33.

As shown in FIG. 5, in the microfluidic chip 2 according to the present embodiment, the bubble trapping region 150 is a recess formed by the curved portion 315 (curved surface 311) of the partition layer 31 and the front surface 10*a* of the substrate 10, and the lower end of the curved surface 311 (edge 102*a*) is the deepest portion. More specifically, the bubble trapping region 150 is a corner formed by the curved surface 311 of the partition layer 31 and the front surface 10*a* of the substrate 10 connected to each other at the edge 102*a*, which is the lower end of the inclined surface 311.

That is, the bubble trapping region 150 is formed on each of the left and right sides on the bottom of the fluidic channel at which the fluidic channel width W22 of the fluidic channel portion 33 is widest. Therefore, by separating air bubbles into the bubble trapping region 150, the air bubbles can be retained in a region away from the center region E1 of the fluidic channel portion 33. With this configuration, the microfluidic chip 2 according to the present embodiment can further improve the stability of fluid flow and further improve the visibility during observation of the interior of the fluidic channel portion 33.

Air bubbles in the fluidic channel portion 33 migrate in the fluid (e.g., reaction solution) from the center region E1 toward the left and right sides of the fluidic channel portion 33 due to pressure or the like when the fluid flows and are collected in the bubble trapping regions 150. As shown in FIG. 5, in the bubble trapping region 150 formed as a corner in this example, the height decreases toward the edge 102*a*, which is the deepest portion.

Accordingly, air bubbles collected in the bubble trapping region 150 are likely to remain in the bubble trapping region 150 and are less likely to leave toward the center region E1 of the channel portion 33.

As shown in FIG. 5, the bubble trapping region 150 is a region formed inside the fluidic channel portion 33 by the partition layer 31 and the substrate 10 and is not formed by attaching a separate member with an adhesive. With this configuration, as with the microfluidic chip 1, the microfluidic chip 2 can improve stability of fluid flow and prevent elution of an adhesive component into a solution in the fluidic channel to suppress inhibition of reaction of the solution.

Thus, the microfluidic chip 2 according to the present embodiment includes the fluidic channel portion 33, the substrate 10 which is the first support member, the cover layer 12 which is the second support member, and a pair of partition layers 31 interposed between the substrate 10 and the cover layer 12 to define the fluidic channel portion 33. Further, the partition layer 31 has the curved portion 315 curved away from the substrate 10 at the edge 102*a* on the fluidic channel portion 33 side of the lower contact surface 102 in contact with the substrate 10. Furthermore, the fluidic channel portion 33 includes the bubble trapping region 150 formed by the curved portion 315 and the front surface 10*a*, which is a surface of the substrate 10 on the fluidic channel portion 33 side, and the bubble trapping region 150 traps air bubbles in the fluidic channel portion 33.

With this configuration, the microfluidic chip 2 can separate air bubbles in a micro fluidic channel into a specific region to improve stability of fluid flow and prevent elution of an adhesive component into a solution in the fluidic channel to suppress inhibition of reaction of the solution.

Further, in the microfluidic chip 2, the fluidic channel width W22 of the fluidic channel portion 33 increases toward the substrate 10 in a region formed by the curved portion 315 of the partition layer 31 and is constant in a region formed by a portion of the partition layer 31 other than the curved portion 315 (region formed by the flat surface 312). With this configuration, the microfluidic chip 2 can ensure the area of the bonding region for bonding the partition layer 31 and the cover layer 12, stabilize fluid flow, and enhance adhesion between the partition layer 31 and the cover layer 12.

Method of Producing Microfluidic Chip

As with the method of producing a microfluidic chip 1 according to the first embodiment (see FIG. 3), the basic method of producing a microfluidic chip 2 according to the present embodiment includes: applying a resin to a substrate 10 (the above S1); exposing the applied resin to light (the above S3); subjecting the exposed resin to development and cleaning to thereby form a partition layer 11 that defines a fluidic channel portion 13 on the substrate 10 (the above S4 and S5); post-baking the partition layer 11 (the above S6); and bonding a cover layer 12 to a side of the partition layer 11 opposite to that facing the substrate 10 (the above S7). Therefore, the detailed description will be omitted.

Also in the present embodiment, as with the microfluidic chip 1, the curved portion 315 and the flat surface (in this example, flat surface 312) may be formed by adjusting the development time, the amount of developer used, and the like in the development process (S4). Further, by removing excess resin (in this example, photosensitive resin) on the substrate 10 in the development process (S4), the partition layer 31 is formed to have the width W21 which decreases toward the substrate 10 in cross-sectional view.

In the present embodiment, in a region on the lower side of the intermediate portion in the thickness direction of the photosensitive resin layer (in this example, the lower side of the intermediate end 310*a*), the curved portion 315 may be formed on a part of the partition layer 31 by adjusting the development time, the concentration of the developer, and the like in development.

For example, in the present embodiment, when forming the upper region 31*a* of the partition layer 31 in development, a constant amount of resin may be dissolved and removed in a partial region from the upper side (side connected to the cover layer 12) of the photosensitive resin layer so that a constant amount of resin remains. Accordingly, the width W21 of the partition layer 31 in the upper region 31*a* of the partition layer 31 can be constant. Further, by adjusting the development time, the concentration of the developer, and the like, the side surface 310 of the upper region 31*a* can be formed in a planar shape as the flat surface 312.

Further, in the remaining region of the photosensitive resin layer (region on the substrate 10 side), the degree of resin dissolution may be increased to increase the amount of resin to be removed as it closer to the substrate 10 so that less resin remains as it closer to the substrate 10. Further, when forming the lower region 31*b* of the partition layer 31 in development, more resin may be dissolved and removed especially at the edge on the fluidic channel portion 33 side of the lower contact surface 102 in contact with the substrate 10 so that less resin remains. Accordingly, in the lower region 31*b*, the curved portion 315 having the curved surface 311 curved in a convex shape curved away from the substrate 10 can be formed, and the width W21 of the partition layer 31 can be decreased toward the substrate 10.

Thus, in the present embodiment, by removing excess resin on the substrate in the development, the curved portion 315 curved in a convex shape at the edge 102*a* on the fluidic channel portion 33 side of the lower contact surface 102 of the partition layer 31 in contact with the substrate 10 can be formed.

Further, in the present embodiment, by forming the photosensitive resin layer using a negative resist, in which an unexposed region dissolves in development, a resin on the lower side of the photosensitive resin layer can be more likely to dissolve in development. Accordingly, the partition layer 31 having the width which increases toward the substrate 10 in cross-sectional view can be more easily formed.

MODIFIED EXAMPLES

Figure 6:
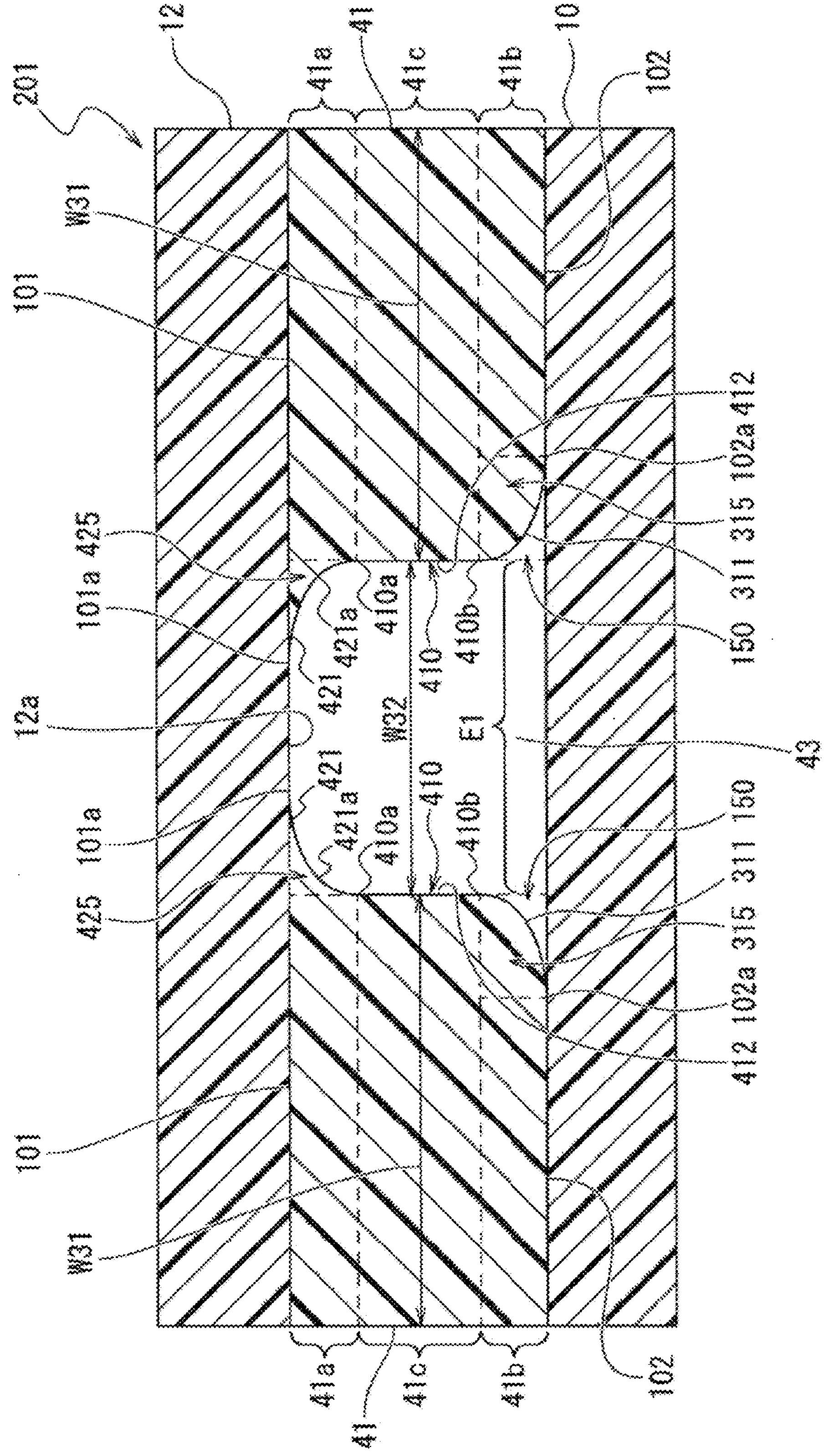
FIG. 6 is a schematic cross-sectional diagram illustrating an example configuration of a microfluidic chip according to a modified example of the present invention.

With reference to FIG. 6, a microfluidic chip according to a modified example of the present embodiment will be described. FIG. 6 is a cross-sectional diagram illustrating an example configuration of a microfluidic chip 201 according to the modified example of the present embodiment.

The microfluidic chip 201 includes a substrate 10, a partition layer 41 that defines a fluidic channel portion 43 on the substrate 10, and a cover layer 12. As shown in FIG. 6, the microfluidic chip 201 differs from the microfluidic chip 2 described above in that an upper region 41*a* of the partition layer 41 has a flared shape of an extension portion 425.

The following description will be given of the partition layer 41 and the fluidic channel portion 43 defined by the partition layer 41. Components other than the partition layer 41 and the fluidic channel portion 43 (substrate 10 and cover layer 12) have the same configuration as the substrate 10 and the cover layer 12 of the microfluidic chip 1, so the same reference signs are used and the description thereof will be omitted.

Shape of Partition Layer and Configuration of Fluidic Channel

In the following description, details of the shape of the partition layer 41 and the configuration of the fluidic channel portion 43 in the microfluidic chip 201 according to this modified example will be described. First, the shape of the partition layer 41 that defines the fluidic channel portion 43 will be described.

As shown in FIG. 6, the partition layer 41 of the microfluidic chip 201 includes the upper contact surface 101, the lower contact surface 102 and a side surface 410. In the partition layer 41 of the microfluidic chip 201, the same configurations as the partition layer 31 of the microfluidic chip 2 are denoted by the same reference signs, and the description thereof will be omitted.

As shown in FIG. 6, the partition layer 41 of the microfluidic chip 201 has the extension portion 425 which extends in a transverse direction of the fluidic channel portion 43 along the rear surface 12*a* of the cover layer 12 which is the second support member, the partition layer 41 having a width increasing toward the second support member (cover layer 12) in cross-sectional view. With this configuration, in the microfluidic chip 201, the area of the bonding region for bonding the partition layer 41 and the cover layer 12 increases. That is, the partition layer 41 has a shape in which a width W31 decreases toward the substrate 10 which is the first support member in cross-sectional view and increases toward the cover layer 12 which is the second support member.

With this configuration, the microfluidic chip 201 can improve stability of fluid flow, prevent elution of an adhesive component into a solution in the fluidic channel to suppress inhibition of reaction of the solution, and enhance adhesion between the partition layer 41 and the cover layer 12.

The "cross-section" in the "cross-sectional view" refers to a cross-section of the microfluidic chip 201 cut in the thickness direction (direction perpendicular to the longitudinal direction of the fluidic channel portion 43), for example, and the cross-section includes the substrate 10, the partition layer 41, the cover layer 12 and the fluidic channel portion 43. In the following description, the shape of the partition layer 41 will be more specifically described.

The side surface 410 is the side surface of the partition layer 41, and a surface defining the fluidic channel portion 43. In this modified example, the edge 101*a* corresponds to the upper end of the side surface 410, and the edge 102*a* corresponds to the lower end of the side surface 410.

As shown in FIG. 6, the curved surface 311 is provided on one end side of the side surface 410. Specifically, as with the microfluidic chip 2, the curved surface 311 is provided on the lower end (edge 102*a*) side of the side surface 410.

Further, a curved surface 421 which is an inclined surface curved in a concave shape is provided on the other end side of the side surface 410. Specifically, the curved surface 421 is provided on the upper end (edge 101*a*) side of the side surface 410. Further, a flat surface 412 is formed in a region of the side surface 410 in which the curved surfaces (curved surfaces 311 and 421) are not provided, that is, a region between the curved surface 311 and the curved surface 421. The partition layer 41 of the microfluidic chip 201 differs from the partition layer 31 of the microfluidic chip 2 in that the side surface 410 of the partition layer 41 has the curved surface 311 and the curved surface 421 at respective ends.

The flat surface 412 is connected to the curved surface 421 at a first intermediate end 410*a* and connected to the curved surface 311 at a second intermediate end 410*b*. That is, the flat surface 412 extends from the first intermediate end 410*a* to the second intermediate end 410*b* of the side surface 410, with the first intermediate end 410*a* corresponding to the upper end of the flat surface 412 and the second intermediate end 410*b* corresponding to the lower end of the flat surface 412.

Further, the inclined surface 421 is connected to the flat surface 412 at the first intermediate end 410*a* of the side surface 410 and connected to the cover layer 12 at the edge 101*a*, which is the upper end of the side surface 410. That is, the curved surface 421 extends from the first intermediate end 410*a* to the edge 101*a* of the side surface 410, with the first intermediate end 410*a* of the side surface 410 corresponding to the lower end of the curved surface 421 and the edge 101*a*, which is the upper end of the side surface 410 corresponding to the upper end of the inclined surface 421.

Further, the curved surface 311 is connected to the flat surface 412 at the second intermediate end 410*b* of the partition layer 41, instead of the intermediate end 310*a* of the partition layer 31 in the microfluidic chip 2. That is, in this modified example, the curved surface 311 extends from the edge 102*b*, which is the lower end of the side surface (in this example, side surface 410) to the second intermediate end 410*b*, and the second intermediate end 410*b* of the side surface 410 corresponds to the lower end of the curved surface 311.

The other configurations of the curved surface 311 of the microfluidic chip 201 according to this modified example are the same as the curved surface 311 of the microfluidic chip 2. Similarly, the curved portion 315 having the curved surface 311 of the microfluidic chip 201 according to this modified example is the same as the curved portion 315 of the microfluidic chip 2.

Detailed description of the curved surface 311 and the curved portion 315 of this modified example will be omitted.

Hereinafter, a region of the partition layer 41 including the curved surface 421 is referred to as an upper region 41*a*, a region including the curved surface 311 is referred to as a lower region 41*b*, and a region including the flat surface 412 is referred to as an intermediate region 41*c*. In FIG. 6, the upper region 41*a*, the lower region 41*b* and the intermediate region 41*c* of the partition layer 41 are divided by a virtual dotted line for ease of understanding. In the partition layer 41, the upper region 41*a*, the lower region 41*b* and the intermediate region 41*c* are preferably formed integrally but may be formed separately. That is, the partition layer 41 may have a multilayer (e.g., three-layer) structure.

The width W31 of the partition layer 41 decreases toward the substrate 10 in the lower region 41*b* which includes the curved surface 311, increases toward the cover layer 12 in the upper region 41*a* which includes the curved surface 421, and is constant in the intermediate region 41*c* which includes the flat surface 412. With this configuration, the microfluidic chip 201 can ensure a region for forming the bubble trapping region 150 in the fluidic channel portion 43 and increase the area of the bonding region for bonding the partition layer 41 and the cover layer 12, while maintaining the width (fluidic channel width W32) of the fluidic channel portion 43 defined by the partition layer 41.

Next, the curved surface 421 provided on the side surface 410 of the partition layer 41 will be specifically described. The curved surface 421 is formed on a part of the remaining side surface 410 (side surface 410 of the upper region 41*a* of the partition layer 41) and curved in a concave shape in cross-sectional view. That is, the curved surface 421 is provided on a region of the side surface 410 on the cover layer 12 side.

As shown in FIG. 6, in the upper region 41*a* of the partition layer 41, the edge 101*a*, which is the upper end of the side surface 410, is located closer to the center of the fluidic channel portion 43 than the first intermediate end 410*a* (lower end of the curved surface 421) is. Specifically, the upper contact surface 101 of the partition layer 41 extends in the direction toward the center of the fluidic channel portion 43 (direction toward the opposing partition layer 41) along the rear surface 12*a* of the cover layer 12. Accordingly, the edge 101*a*, which is the upper end of the side surface 410 is located closer to the opposing partition layer 41 than the first intermediate end 410*a* is.

In other words, in the partition layer 41, the lower end of the curved surface 421 (first intermediate end 410*a*) is located further away from the center of the fluidic channel portion 43 than the upper end of the curved surface 421 (edge 101*a*) is. That is, the lower end of the curved surface 421 is located further away from the opposing partition layer 41 than the edge 101*a*, which is the upper end of the curved surface 421, is.

The curved surface 421 is curved in a concave shape from the first intermediate end 410*a* to the edge 101*a*, where it is connected to the cover layer 12. Thus, the width W31 of the partition layer 41 increases in the direction toward the center of the fluidic channel portion 43, that is, toward the opposing partition layer 41 (in the transverse direction of the fluidic channel portion 43), as it approaches the cover layer 12. Therefore, the width W31 of the partition layer 41 in cross-sectional view increases toward the cover layer 12.

The width W31 of the upper region 41*a* of the partition layer 41 continuously increases toward the cover layer 12. More specifically, the width W31 of the upper region 41*a* of the partition layer 41 continuously expands and increases toward the center of the fluidic channel portion 43, that is, in the transverse direction, as it approaches the cover layer 12. The "continuously increases (expands)" herein means that the width W31 of the partition layer 41 continuously increases (expands), without decreasing (reducing), from the first intermediate end 410*a*, which is the lower end of the curved surface 421, to the edge 101*a*, which is the upper end of the curved surface 421.

As shown in FIG. 6, in the curved surface 421 curved in a concave shape, a deepest portion 421*a* is located closer to the center of the fluidic channel portion 43 than the first intermediate end 410*a*, which is the lower end of the curved surface 421, is. Therefore, the width W31 of the partition layer 41 continuously increases, without decreasing, even in the deepest portion 421*a* of the curved surface 421. With this configuration, in the microfluidic chip 201, the area of the bonding region for bonding the partition layer 41 and the cover layer 12 can be reliably increased, further reliably enhancing adhesion between the partition layer 41 and the cover layer 12.

As shown in FIG. 6, the partition layer 41 has the extension portion 425 which extends in a transverse direction of the fluidic channel portion 43 along the rear surface 12*a* of the cover layer 12, the partition layer 41 having a width increasing toward the cover layer 12, which is the second support member, in cross-sectional view. Specifically, the extension portion 425 extends in the direction toward the center of the fluidic channel portion 43, that is, toward the opposing partition layer 41. Accordingly, the extension portion 425 has a flared shape, and the width of the partition layer 41 increases toward the cover layer 12.

The extension portion 425 has the curved surface 421 curved in a concave shape in cross-sectional view. Accordingly, the extension portion 425 has a shape in which the thickness decreases in the transverse direction of the fluidic channel portion 43. With this configuration, compared with the case where the curved surface 421 has a planar shape, the microfluidic chip 201 can reduce a decrease in the width (fluidic channel width W32) of the fluidic channel portion 43 due to an increase in the width W31 of the partition layer 41, while increasing the area of the bonding region for bonding the partition layer 41 and the cover layer 12.

As described above, in the microfluidic chip 201 according to this modified example, the partition layer 41 has the extension portion 425 which extends in a transverse direction of the fluidic channel portion 43 along the front surface of the second support member (cover layer 12), the partition layer 41 having a width increasing toward the second support member (cover layer 12) in cross-sectional view.

With this configuration, the microfluidic chip 201 can improve stability of fluid flow, prevent elution of an adhesive component into a solution in the fluidic channel to suppress inhibition of reaction of the solution, and enhance adhesion between the partition layer 41 and the cover layer 12.

In the partition layer 41, the extension portion 425 has the curved surface 421 curved in a concave shape in cross-sectional view.

With this configuration, the microfluidic chip 201 can reduce a decrease in the width (fluidic channel width W32) of the fluidic channel portion 43 due to an increase in the width W31 of the partition layer 41, further improve stability of fluid flow, and enhance adhesion between the partition layer 41 and the cover layer 12.

Next, the configuration of the fluidic channel portion 43 defined by the substrate 10, the partition layer 41 and the cover layer 12 will be described. The fluidic channel width W32 of the fluidic channel portion 43 is defined as the width between a pair of partition layers 41 facing each other, that is, the width between the side surfaces 410.

As described above, the width W31 of the partition layer 41 in cross-sectional view decreases toward the substrate 10 and increases toward the substrate 12. Accordingly, as shown in FIG. 6, the width between the side surfaces 410 of the pair of partition layers 41 is wider on the substrate 10 side than between the flat surfaces 412 and narrower on the cover layer 12 side than between the flat surfaces 412. Therefore, the fluidic channel width W32 of the fluidic channel portion 43 increases toward the substrate 10 and decreases toward the cover layer 12 from the center region in the height of the fluidic channel portion 43 (thickness of the partition layer 41).

Specifically, the fluidic channel width W32 is widest at the lowest part (bottom) of the fluidic channel portion 43 where the front surface 10*a* of the substrate 10 is exposed, that is, between the lower ends (edges 102*a*) of the side surfaces 410 of the pair of partition layers 41. This is similar to the structure of the microfluidic chip 2 described above, in which the fluidic channel width W22 is widest at the bottom of the fluidic channel portion 33 (between the edges 102*a* of the pair of partition layers 31).

Further, the fluidic channel width W32 is narrowest at the top of the fluidic channel portion 43 where the rear surface 12*a* of the cover layer 12 is exposed, that is, between the upper ends (edges 101*a*) of the side surfaces 410 of the pair of partition layers 41.

As described above, the width W31 of the partition layer 41 continuously increases toward the cover layer 12 in the upper region 41*a* which includes the curved surface 421 extending from the first intermediate end 410*a* to the upper end (edge 101*a*) of the side surface 410. Specifically, in the pair of partition layers 41 facing each other, each of the extension portions 425, which include the curved surface 421, approaches the other in the transverse direction of the fluidic channel portion 43.

Accordingly, the width between the extension portions 425 of the pair of partition layers 41 becomes narrower (decreases) toward the cover layer 12. That is, the width of the fluidic channel portion 43 (fluidic channel width W32) decreases toward the cover layer 12 in a region formed by the extension portion 425 of the partition layer 41. More specifically, the width between the curved surfaces 421 of the pair of partition layers 41 becomes continuously narrower (decreases) toward the cover layer 12. That is, the fluidic channel width W32 between the curved surfaces 421 of the pair of partition layers 41 becomes continuously narrower (decreases) toward the cover layer 12.

The "continuously decreases" herein means that the fluidic channel width W32 of the fluidic channel portion 43 continuously decreases, without increasing, from a region between the upper ends of the flat surfaces 412 (region between the first intermediate ends 410*a*) toward the top of the fluidic channel portion 43 (between the edges 101*a*).

As described above, the width W31 of the partition layer 41 is constant in the intermediate region 41*c* which includes the flat surface 412 extending from the first intermediate end 410*a* to the second intermediate end 410*b* of the side surface 410. Accordingly, the width between the flat surfaces 412 in the pair of partition layers 41 is constant. That is, the fluidic channel width W32 between the flat surfaces 412 (between the intermediate regions 41*c*) of the pair of partition layers 41 is constant. More specifically, the fluidic channel width W32 between the flat surfaces 412 is narrower than between the curved surfaces 311 (between the lower regions 41*b*) and wider than between the curved surfaces 421 (between the upper regions 41*a*).

Thus, the width of the fluidic channel portion 43 increases toward the substrate 10 in a region formed by the curved portion 315 of the partition layer 41, more specifically, a region formed by the curved surface 311, and is constant in a region formed by the flat surface 412 of the partition layer 41.

Further, the width of the fluidic channel portion 43 (fluidic channel width W32) decreases toward the cover layer 12 in a region formed by the extension portion 425 of the partition layer 41.

With this configuration, a region with the reduced width W31 of the partition layer 41 can be limited to the substrate 10 side, that is, the lower region 41*b* of the partition layer 41, and the width W31 of the partition layer 41 can be increased in the upper region 41*a* of the partition layer 41. Accordingly, the microfluidic chip 201 can increase the area of the bonding region for bonding the partition layer 41 and the cover layer 12, while ensuring the width of the fluidic channel width W32 sufficient to form the bubble trapping region 150 in a region between the curved surfaces 311 of the pair of partition layers 41. Therefore, the microfluidic chip 201 can enhance adhesion between the partition layer 41 and the cover layer 12, while separating air bubbles in a micro fluidic channel into a specific region (bubble trapping region 150) to improve the stability of fluid flow.

Further, the fluidic channel width W32 is constant in a region formed by the flat surface 412 and is wider than a region formed by the extension portion 425. With this configuration, a region with the reduced fluidic channel width W32 can be limited to a region on the top side (cover layer 12 side) of the fluidic channel portion 43, that is, between the curved surfaces 421. Accordingly, in the microfluidic chip 201, the area of the bonding region for bonding the partition layer 41 and the cover layer 12 can be reliably increased, while maintaining the width of the fluidic channel width W32 of the fluidic channel portion 43 in a region between the flat surfaces 412 of the pair of partition layers 41. Therefore, the microfluidic chip 201 can reliably enhance adhesion between the partition layer 41 and the cover layer 12, while improving flow stability of a fluid (e.g., reaction solution) in the fluidic channel portion 43 and visibility during observation of the interior of the fluidic channel portion 43.

Further, as shown in FIG. 6, the fluidic channel portion 43 has a rounded corner shape in cross-sectional view in a region between the upper regions 41*a* of the pair of partition layers 41, that is, a region between the curved surfaces 421. The "cross-section" in the "cross-sectional view" refers to a cross-section of the microfluidic chip 201 cut in the thickness direction (direction perpendicular to the longitudinal direction of the fluidic channel portion 43), and the cross-section includes the substrate 10, the partition layer 41, the cover layer 12 and the fluidic channel portion 43. Since the fluidic channel portion 43 has a rounded corner shape in cross-sectional view in a region between the curved surfaces 421, a fluid flow speed and a flow rate of a fluid (e.g., reaction solution) in the fluidic channel portion 43 can be stabilized.

In the microfluidic chip 201 according to this modified example, the fluidic channel portion 43 includes the bubble trapping region 150 that traps air bubbles in the fluidic channel portion 43. As shown in FIG. 6, the bubble trapping region 150 is formed by the curved portion 315 (specifically, curved surface 311) of the partition layer 41 and the front surface 10*a* which is the surface of the substrate 10 on the fluidic channel portion 43 side. The bubble trapping region 150 in the microfluidic chip 201 has the same configuration as the bubble trapping region 150 in the microfluidic chip 2, and detailed description thereof will be omitted.

Method of Producing Microfluidic Chip

The basic method of producing a microfluidic chip 201 according to this modified example is the same as the method of producing a microfluidic chip 2, and detailed description will be omitted.

In this modified example, the upper region 41*a* of the partition layer 41 can be formed in a shape having the width W31 which increases toward the cover layer 12 in cross-sectional view by adjusting the wavelength of ultraviolet light during exposure in the exposure process (S3) and removing excess resin from the photosensitive resin layer in the development process (S4).

Figure 7:
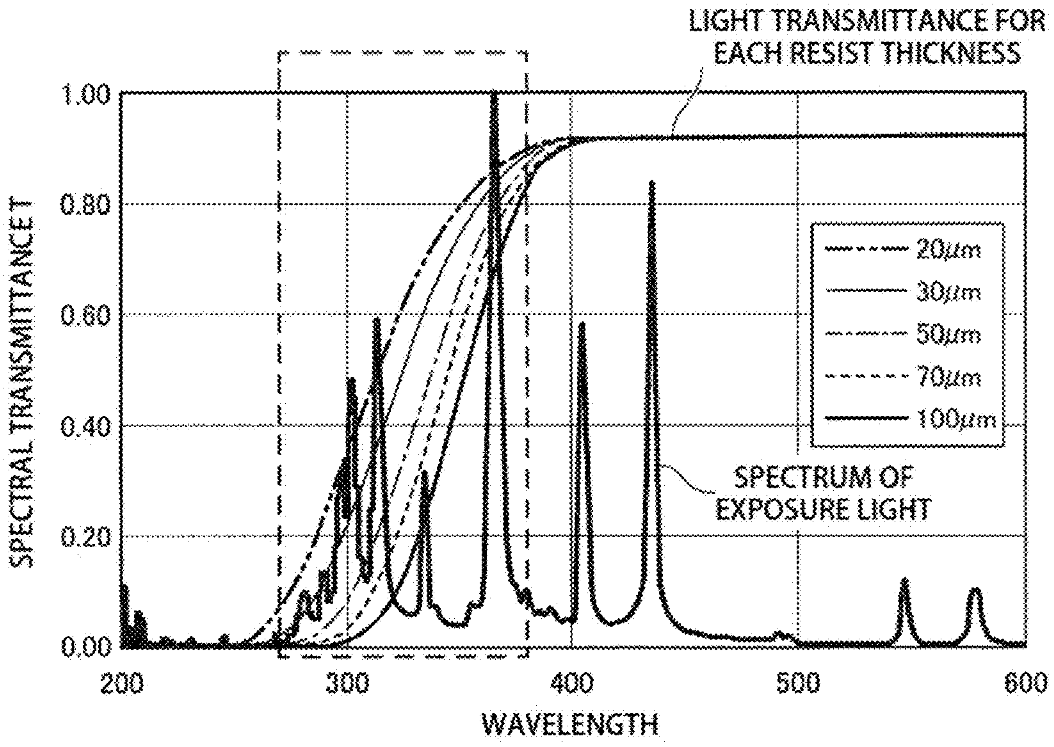
FIG. 7 is a line graph showing an example of light transmittance of a photosensitive resin layer.

As an example, a case where the photosensitive resin layer for forming the partition layer 41 is formed of a negative resist will be described with reference to FIG. 7. FIG. 7 is a line graph showing the light transmittance (in this example, ultraviolet light transmittance) of a photosensitive resin layer formed of a negative resist, and an example of spectrum (transmission spectrum) of exposure light (in this example, ultraviolet light) emitted from an exposure device.

In FIG. 7, the light transmittance of the photosensitive resin layer is shown for each film thickness (20 μm to 100 μm).

As shown in FIG. 7, in this example, the peak of the spectrum of exposure light is present in a specific wavelength range indicated by the dotted line frame. Further, in this example, the transmittance to light in the specific wavelength range differs depending on the film thickness. In this case, in the photosensitive resin layer during the exposure process, the amount of exposure decreases relatively from the surface toward the inside of the photosensitive resin layer. Specifically, the amount of exposure to light (ultraviolet light) in the specific wavelength range indicated by the dotted line frame in FIG. 7 decreases toward the inside of the photosensitive resin layer.

The light in a specific wavelength range described herein may correspond to, for example, ultraviolet light in the wavelength range of 250 nm or greater and 350 nm or less in the ultraviolet light region. For example, FIG. 7 shows that the transmittance to ultraviolet light in the specific wavelength range decreases as the film thickness of the photosensitive resin layer increases. In other words, the light transmittance of a portion with thin film thickness, that is, a surface portion (upper part) of the photosensitive resin layer, indicates that the amount of exposure is greater than in the inside (lower part) of the photosensitive resin layer.

The fact that the amount of exposure is greater in the upper part of the photosensitive resin layer indicates that the resin (negative resist) is more easily cured in the upper part of the photosensitive resin layer (the side bonded to the cover layer 12). Accordingly, more resin remains without being dissolved during development in the upper part of the photosensitive resin layer. That is, by exposing the photosensitive resin on the substrate 10 to light in the specific wavelength range (light having a wavelength of 250 nm or greater and 350 nm or less in the ultraviolet light region) in the exposure process (S3) and removing excess resin on the substrate 10 by the development, the partition layer 41 can be formed to have a width which increases toward the cover layer 12 in cross-sectional view, on a side of the partition layer 41 opposite to that facing the substrate 10. That is, the width W31 of the partition layer 41 can be increased toward the cover layer 12, and the upper region of the partition layer 41 can be formed in a flared shape.

Further, by dissolving a resin on the lower side of the cured resin in the photosensitive resin layer and removing excess resin during development, the curved surface 421 curved in a concave shape can be formed on the side surface 410 of the partition layer 41. In this process, the curved surface 421 curved in a concave shape in cross-sectional view can be formed on a portion of the side surface 410 of the upper region 41*a* of the partition layer 41 by adjusting, for example, the development time and the amount of the developer used in development. Therefore, the curved surface 421 with one end (edge 101*a*) being in contact with the cover layer 12 can be formed by development on a part of the side surface 410 of the upper region 41*a* of the partition layer 41 (side surface 410 of the upper region 41*a*). Accordingly, the extension portion 425 including the curved surface 421 can be formed in the upper region 41*a* of the partition layer 41.

Although detailed description is omitted, the curved surface 311 may be formed on the lower region 41*b* of the partition layer 41, and the flat surface (in this example, flat surface 412) may be formed on the intermediate region 41*c* of the partition layer 41, by development in the same manner as in the method of producing a microfluidic chip 2. Thus, the microfluidic chip 201 can be obtained in which the width W31 of the lower region 41*b* decreases in cross-sectional view toward the substrate 10 which is the first support member, the width W31 of the upper region 41*a* increases in cross-sectional view toward the cover layer 12 which is the second support member, and the width W31 of the intermediate region 41*c* is constant.

Third Embodiment

Configuration of Microfluidic Chip

Figure 8:
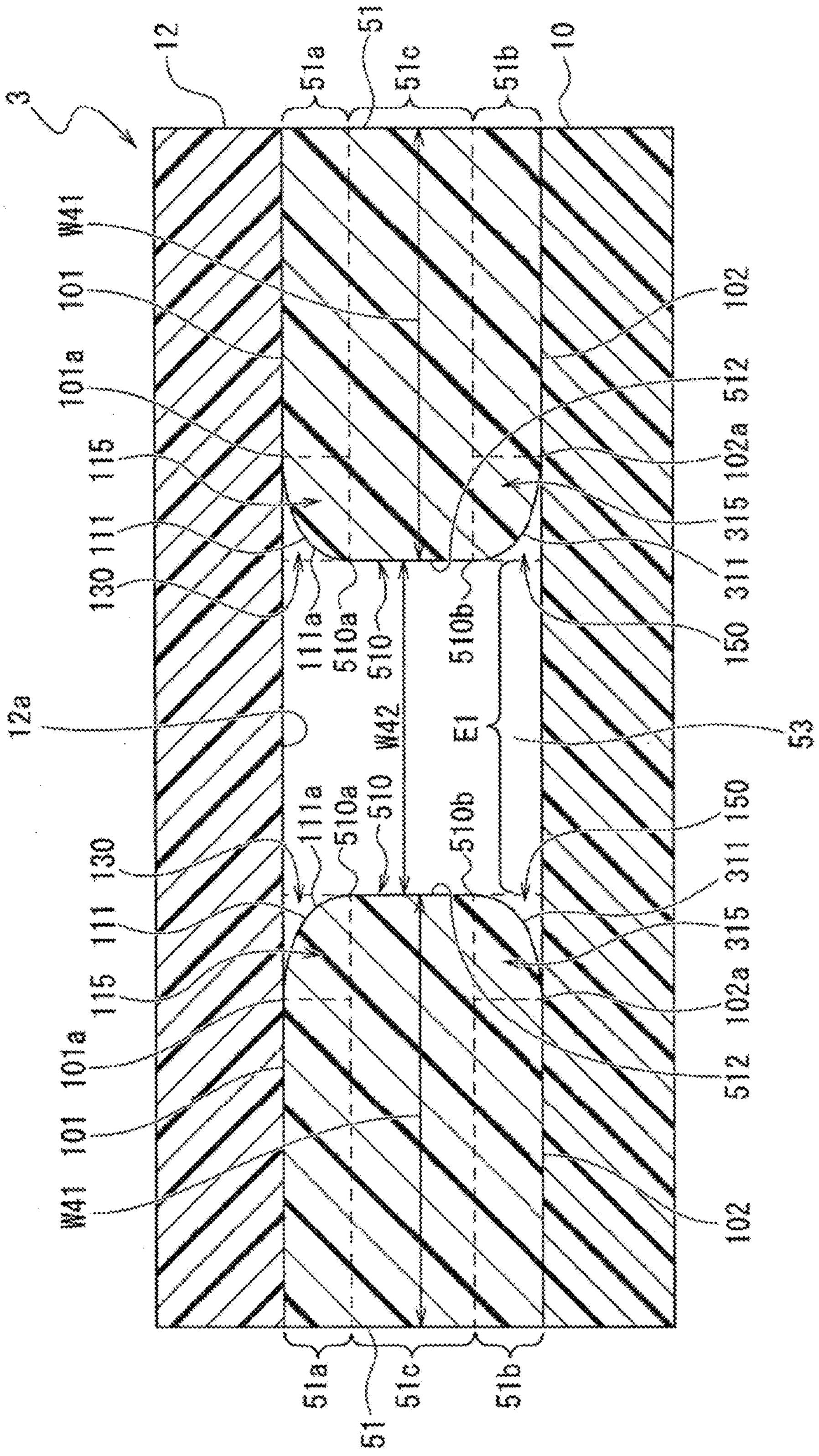
FIG. 8 is a schematic cross-sectional diagram illustrating an example configuration of a microfluidic chip according to a third embodiment of the present invention.

With reference to FIG. 8, a microfluidic chip according to a third embodiment of the present invention will be described. FIG. 8 is a cross-sectional diagram illustrating an example configuration of a microfluidic chip 3 according to the third embodiment of the present invention.

Overview of Microfluidic Chip

As shown in FIG. 8, the microfluidic chip 3 differs from the microfluidic chips 1 and 2 according to the first and second embodiments in that multiple curved surfaces (curved surfaces 115 and 315) are provided on a side surface 510 of a partition layer 51. The following description will be given of the partition layer 51 and a fluidic channel portion 53 defined by the partition layer 51 in the microfluidic chip 3.

The substrate 10 and cover layer 12 in the microfluidic chip 3 have the same configuration as the substrate 10 and the cover layer 12 of the microfluidic chip 1, so the same reference signs are used and the description thereof will be omitted.

As shown in FIG. 8, in the microfluidic chip 3, the fluidic channel portion 53, which is a fluidic channel through which a fluid flows, is defined by walls sandwiched between two support members (first and second support members). In this example, as with the microfluidic chip 1 according to the first embodiment, the cover layer 12 corresponds to the first support member, and the substrate 10 corresponds to the second support member.

Shape of Partition Layer and Configuration of Fluidic Channel

In the following description, details of the shape of the partition layer 51 and the configuration of the fluidic channel portion 53 in the microfluidic chip 3 according to the present embodiment will be described. First, the shape of the partition layer 51 that defines the fluidic channel portion 53 will be described.

As shown in FIG. 8, the partition layer 51 has a curved portion 115 (an example of first curved portion) provided on the first support member (in this example, cover layer 12), and a curved portion 315 (an example of second curved portion) curved in a direction away from the substrate 10 (in this example, substrate 10) at an edge on the fluidic channel portion 53 side of the lower contact surface 102 in contact with the second support member, which is the second support member. The fluidic channel portion 53 includes a bubble trapping region 130 (an example of first bubble trapping region) formed by the curved portion 115 and the rear surface 12*a* of the cover layer 12 which is the first support member, the bubble trapping region 130 trapping air bubbles in the fluidic channel portion 53, and a bubble trapping region 150 (an example of second bubble trapping region) formed by the curved portion 315 and the front surface 10*a*, which is a surface of the substrate 10 as the second support member on the fluidic channel portion 53 side, the bubble trapping region 150 traps air bubbles in the fluidic channel portion 53.

Since the microfluidic chip 3 includes bubble trapping regions (bubble trapping regions 130 and 150), it can more reliably separate air bubbles in the fluidic channel portion 53 into a specific region to further improve stability of fluid flow and prevent elution of an adhesive component into a solution in the fluidic channel to suppress inhibition of reaction of the solution.

As shown in FIG. 8, the partition layer 51 of the microfluidic chip 3 includes the upper contact surface 101, the lower contact surface 102 and a side surface 510.

In the partition layer 51 of the microfluidic chip 3, the same configurations as the partition layers 11 and 31 of the microfluidic chips 1 and 2 are denoted by the same reference signs, and the description thereof will be omitted.

The side surface 510 is the side surface of the partition layer 51, and a surface defining the fluidic channel portion 53. In the present embodiment, the edge 101*a* corresponds to the upper end of the side surface 510, and the edge 102*a* corresponds to the lower end of the side surface 510.

As shown in FIG. 8, the curved surface 111 is provided on one end side of the side surface 510. Specifically, as with the microfluidic chip 1, the curved surface 111 is provided on the upper end (edge 101*a*) side of the side surface (in this example, side surface 510) of the partition layer. Further, the curved surface 311 is provided on the other end side of the side surface 510. Specifically, as with the microfluidic chip 2, the curved surface 311 is provided on the lower end (edge 102*a*) side of the side surface (in this example, side surface 510) of the partition layer.

Further, a flat surface 512 is formed in a region of the side surface 510 in which the curved surfaces (curved surfaces 111 and 311) are not provided, that is, a region between the curved surface 111 and the curved surface 311. The partition layer 51 of the microfluidic chip 3 differs from the partition layers 11 and 31 of the microfluidic chips 1 and 2 in that the side surface 510 of the partition layer 51 has the curved surfaces 111 and 311 at respective ends.

The flat surface 512 is connected to the curved surface 111 at a first intermediate end 510*a* and connected to the curved surface 311 at a second intermediate end 510*b*. That is, as with the flat surfaces (flat surfaces 212 and 412) of the microfluidic chips 103 and 201, the flat surface 512 extends from the first intermediate end (in this example, first intermediate end 510*a*) to the second intermediate end (in this example, second intermediate end 510*b*) of the side surface (in this example, side surface 510).

In the present embodiment, the first intermediate end 510*a* corresponds to the upper end of the flat surface 512, and the second intermediate end 510*b* corresponds to the lower end of the flat surface 512.

The curved surface 111 is connected to the flat surface 512 at the first intermediate end 510*a* of the partition layer 51, instead of the intermediate end 110*a* of the partition layer 11 in the microfluidic chip 1. That is, in the present embodiment, the curved surface 111 extends from the edge 101*a*, which is the upper end of the side surface (in this example, side surface 510) to the first intermediate end 510*a*, and the first intermediate end 510*a* of the side surface 510 corresponds to the lower end of the curved surface 111. The other configurations of the curved surface 111 and the curved portion 115 having the curved surface 111 of the microfluidic chip 3 according to the present embodiment are the same as the curved portion 115 having the curved surface 111 of the microfluidic chip 1.

Further, the curved surface 311 of the partition layer 51 is connected to the flat surface 512 at the second intermediate end 510*b* of the partition layer 51, instead of the intermediate end 310*a* of the partition layer 31 in the microfluidic chip 2. That is, in the present embodiment, the curved surface 311 extends from the edge 102*a*, which is the lower end of the side surface (in this example, side surface 510) to the second intermediate end 510*b*, and the second intermediate end 510*b* of the side surface 510 corresponds to the upper end of the curved surface 311. The other configurations of the curved surface 311 and the curved portion 315 having the curved surface 311 of the microfluidic chip 3 according to the present embodiment are the same as the curved portion 315 having the curved surface 311 of the microfluidic chip 2.

Further, the flat surface 512 of the present embodiment has the same configuration as the flat surface (flat surfaces 212 and 412) of the microfluidic chips 103 and 201.

Detailed description of the curved surfaces 111 and 311, the curved portions 115 and 315, and the flat surface 512 of the present embodiment will be omitted.

Hereinafter, a region of the partition layer 51 including the curved surface 111 is referred to as an upper region 51*a*, a region including the curved surface 311 is referred to as a lower region 51*b*, and a region including the flat surface 512 is referred to as an intermediate region 51*c*. In FIG. 8, the upper region 51*a*, the lower region 51*b* and the intermediate region 51*c* of the partition layer 51 are divided by a virtual dotted line for ease of understanding. In the partition layer 51, the upper region 51*a*, the lower region 51*b* and the intermediate region 51*c* are preferably formed integrally but may be formed separately. That is, the partition layer 51 may have a multilayer (e.g., three-layer) structure.

The width W41 of the partition layer 51 decreases toward the cover layer 12 in the upper region 51*a* which includes the curved surface 111, decreases toward the substrate 10 in the lower region 51*b* which includes the curved surface 311, and is constant in the intermediate region 51*c* which includes the flat surface 512. With this configuration, the microfluidic chip 3 can ensure a region for forming the bubble trapping regions 130 and 150 in the fluidic channel portion 53.

Next, the configuration of the fluidic channel portion 53 defined by the substrate 10, the partition layer 51 and the cover layer 12 will be described. A fluidic channel width W42 of the fluidic channel portion 53 is defined as the width between a pair of partition layers 51 facing each other, that is, the width between the side surfaces 510.

As described above, the width W41 of the partition layer 51 in cross-sectional view decreases toward each of the cover layer 12 and the substrate 10. Accordingly, as shown in FIG. 8, the width between the side surfaces 510 of the pair of partition layers 51 is wider on the cover layer 12 side and the substrate 10 side than between the flat surfaces 512 and narrowest between the flat surfaces 512. Therefore, the fluidic channel width W42 of the fluidic channel portion 53 increases from the center region in the height of the fluidic channel portion 53 (thickness of the partition layer 51) toward each of the cover layer 12 and the substrate 10 and is narrower in the center region than the other regions.

Specifically, the width of the fluidic channel portion 53 (fluidic channel width W42) increases toward the cover layer 12, which is the first support member, in a region formed by the curved portion 115 of the partition layer 51 (region formed by the curved surface 111 of the side surface 510). Further, the fluidic channel width W42 increases toward the substrate 10, which is the second support member, in a region formed by the curved portion 315 of the partition layer 51 (region formed by the curved surface 311 of the side surface 510).

More specifically, the fluidic channel width W42 is widest at the top of the fluidic channel portion 53 where the rear surface 12*a* of the cover layer 12 is exposed and the lowest part (bottom) of the fluidic channel portion 53 where the front surface 10a of the substrate 10 is exposed. That is, the fluidic channel width W42 is widest between the upper and lower ends (edges 101a and 102a) of the side surfaces 510 of the pair of partition layers 51. This is similar to the structure of the microfluidic chip 1, in which the fluidic channel width W2 at the top of the fluidic channel portion 13 is widest and the structure of the microfluidic chip 2, in which the fluidic channel width W22 at the bottom of the fluidic channel portion 33 is widest.

As shown in FIG. 8, in the microfluidic chip 3 according to the present embodiment, the fluidic channel portion 53 includes the bubble trapping regions 130 and 150. With this configuration, the microfluidic chip 3 can more reliably separate air bubbles in the fluidic channel portion 53 into specific regions to improve stability of fluid flow and prevent elution of an adhesive component into a solution in the fluidic channel to suppress inhibition of reaction of the solution.

The bubble trapping regions 130 and 150 in the microfluidic chip 3 have the same configuration as the bubble trapping regions 130 and 150 in the microfluidic chips 1 and 2, and detailed description thereof will be omitted.

Method of Producing Microfluidic Chip

The basic method of producing a microfluidic chip 3 according to the present embodiment is the same as the method of producing a microfluidic chip 1 according to the first embodiment described above (see FIG. 3), and detailed description will be omitted. Also in the present embodiment, as with the microfluidic chips 1 and 2, the curved portion 115, the flat surface (in this example, flat surface 512), and the curved portion 315 may be formed by adjusting the development time, the amount of developer used, and the like in the development process (S4).

For example, in the present embodiment, by removing excess resin (in this example, photosensitive resin) on the substrate in the development, the curved portion 115 (an example of upper curved portion) curved in a convex shape at the edge 101a on the fluidic channel portion 53 side of the upper contact surface 101 of the partition layer 51 in contact with the cover layer 12 may be formed. Further, by removing excess resin on the substrate in the development, the curved portion 315 (lower curved portion) curved in a convex shape at the edge 102a on the fluidic channel portion 53 side of the lower contact surface 102 of the partition layer 51 in contact with the substrate 10 can be formed.

Thus, by removing excess resin (in this example, photosensitive resin) on the substrate 10, the partition layer 51 can be formed to have the width W41 which decreases toward each of the cover layer 12 and the substrate 10 in cross-sectional view.

For example, when the photosensitive resin layer is formed of a positive resist, the amount of exposure in the upper part of the photosensitive resin layer (positive resist layer) can be the same as that in the lower part (on the substrate 10 side) by adjusting the exposure direction of ultraviolet light or by focusing light emitted from the exposure device during exposure. Accordingly, the amount of resin that dissolves during development in the upper and lower parts of the photosensitive resin layer increases. On the other hand, less resin dissolves during development in the intermediate portion of the photosensitive resin layer where the amount of exposure is low, compared with the upper and lower parts, resulting in a smaller amount of resin remaining.

Accordingly, the width W41 of the upper region 51a and the lower region 51b of the partition layer 51 can be decreased toward the cover layer 12 and the substrate 10, respectively, so that the width W41 of the partition layer 51 in the intermediate region 51c of the partition layer 51 becomes larger than the upper region 51a and the lower region 51b.

In the present embodiment, the partition layer formed of the photosensitive resin layer may have a bilayer structure of a positive resist and a negative resist. Specifically, a negative resist is applied to the substrate 10, exposed and developed to form the lower region 51b having the curved portion 315 (lower curved portion). Then, a positive resist is applied to the lower region 51b, exposed and developed to form the upper region 51a having the curved portion 115 (upper curved portion). Thus, the partition layer 51 may have a bilayer structure. When forming the lower region 51b, in the region of the photosensitive resin layer formed of the negative resist on the substrate 10 side, the closer to the substrate 10, the lower the amount of exposure and the more the resin dissolves, and the smaller the amount of resin remaining during development. Further, when forming the upper region 51a, in the region of the photosensitive resin layer formed of the positive resist on the cover layer 12 side, more resin dissolves due to a larger amount of exposure, and a decreased amount of resin remains during development. Accordingly, the width W41 of the partition layer 51 in the upper region 51a and the lower region 51b can be decreased toward the cover layer 12 and the substrate 10. Also in this case, the flat surface 512 may be provided by development on the side surface 510 between the curved portion 315 and the curved portion 115 to form the intermediate region 51c.

Fourth Embodiment

Overview of Microfluidic Chip

Figure 9:
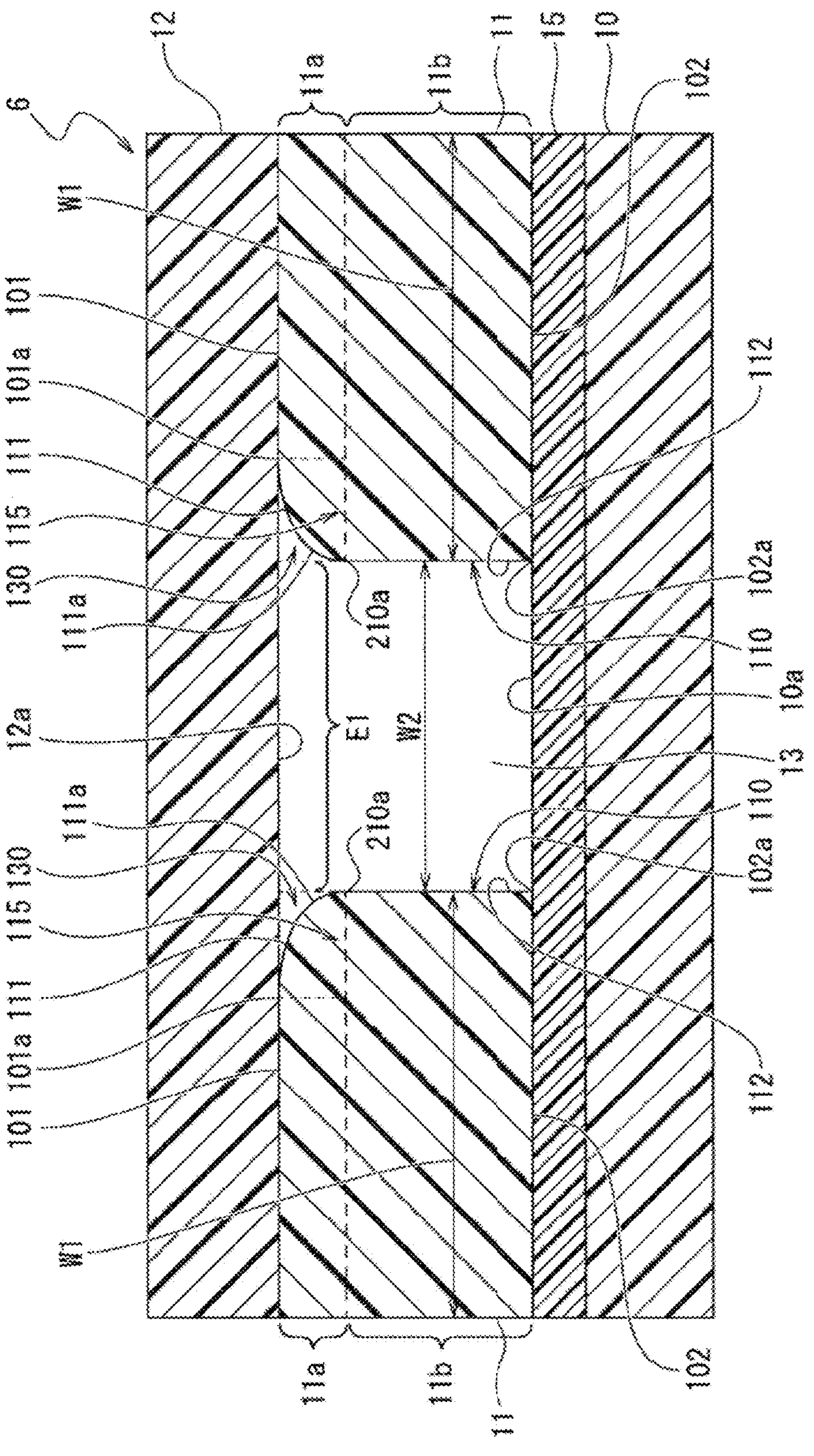
FIG. 9 is a schematic cross-sectional diagram illustrating an example configuration of a microfluidic chip according to a fourth embodiment of the present invention.

With reference to FIG. 9, a microfluidic chip 6 according to a fourth embodiment of the present invention will be described. FIG. 9 is a cross-sectional diagram illustrating an example configuration of a microfluidic chip 6 according to the fourth embodiment of the present invention.

The microfluidic chip 6 includes a substrate 10, an adhesive layer 15 disposed on the substrate 10, a partition layer 11 that defines a fluidic channel portion 13 on the substrate 10, and a cover layer 12. That is, the microfluidic chip 6 differs from the microfluidic chip 1 according to the first embodiment in that the adhesive layer 15 is provided between the partition layer 11 and the substrate 10.

Configuration of Adhesive Layer

The adhesive layer 15 will be described below. Components other than the adhesive layer 15 (substrate 10, partition layer 11, cover layer 12 and fluidic channel portion 13) have the same configuration as in the microfluidic chip 1, so the same reference signs are used and the description thereof will be omitted.

In the microfluidic chip 6, the substrate 10 may be subjected to hydrophobic surface treatment (HMDS treatment) or may be coated with a thin film of resin in order to enhance adhesion between the substrate 10 and a resin layer (for example, photosensitive resin layer), that is, the partition layer 11. In particular, when glass or the like is used for the substrate 10, the adhesive layer 15 formed of a thin film may be provided between the substrate 10 and the partition layer 11 (photosensitive resin layer) as shown in FIG. 9. In this case, a fluid (for example, liquid) flowing through the fluidic channel portion 13 comes into contact with the adhesive layer 15 instead of the substrate 10. Therefore, the adhesive layer 15 may be resistant to the fluid introduced into the fluidic channel portion 13. The adhesive layer 15 provided on the substrate 10 can contribute to improving the resolution of the fluidic channel pattern of the photosensitive resin.

MODIFIED EXAMPLES

With reference to FIGS. 10 to 13, a microfluidic chip according to a modified example of the present embodiment will be described.

First Modified Example

Figure 10:
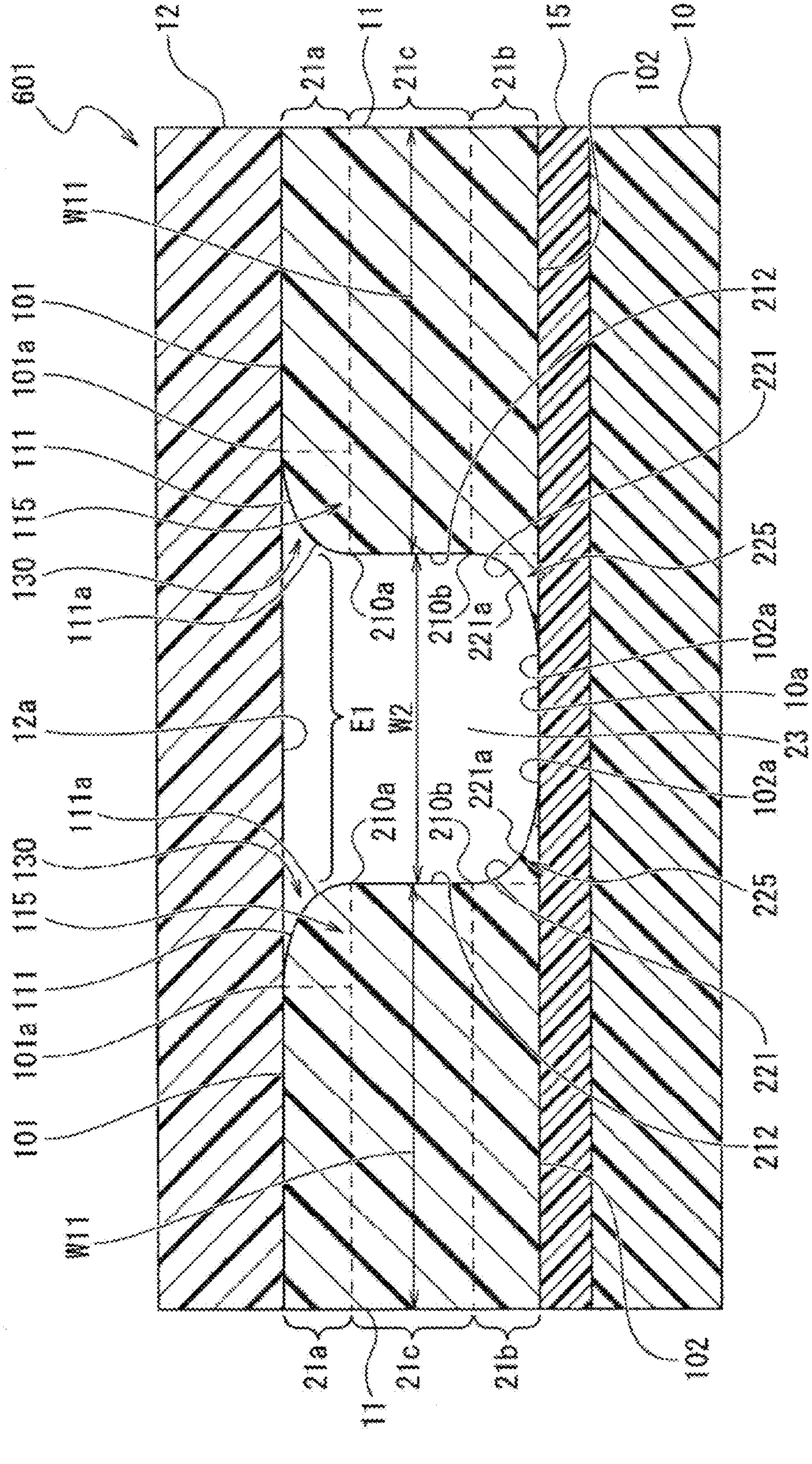
FIG. 10 is a schematic cross-sectional diagram illustrating an example configuration of a microfluidic chip according to a first modified example of the fourth embodiment of the present invention.

First, referring to FIG. 10, a configuration of a microfluidic chip 601 according to a first modified example of the present embodiment will be described. FIG. 10 is a schematic cross-sectional diagram illustrating an example configuration of the microfluidic chip 601 according to this modified example. The microfluidic chip 601 has a configuration in which an adhesive layer is additionally provided in the microfluidic chip 103 according to the modified example of the first embodiment.

The microfluidic chip 601 includes a substrate 10, an adhesive layer 15 disposed on the substrate 10, a partition layer 21 that defines a fluidic channel portion 23 on the substrate 10, and a cover layer 12. That is, the microfluidic chip 601 differs from the microfluidic chip 103 according to the first modified example of the first embodiment in that the adhesive layer 15 is provided between the partition layer 21 and the substrate 10.

The adhesive layer 15 in this modified example is the same as the adhesive layer 15 in the microfluidic chip 6 according to the fourth embodiment described above, and the description thereof will be omitted. Providing the adhesive layer 15 can enhance the adhesion between the substrate 10 and a resin layer (for example, photosensitive resin layer), that is, the partition layer 21, in the microfluidic chip 601.

(4.3.2) Second Modified Example

Figure 11:
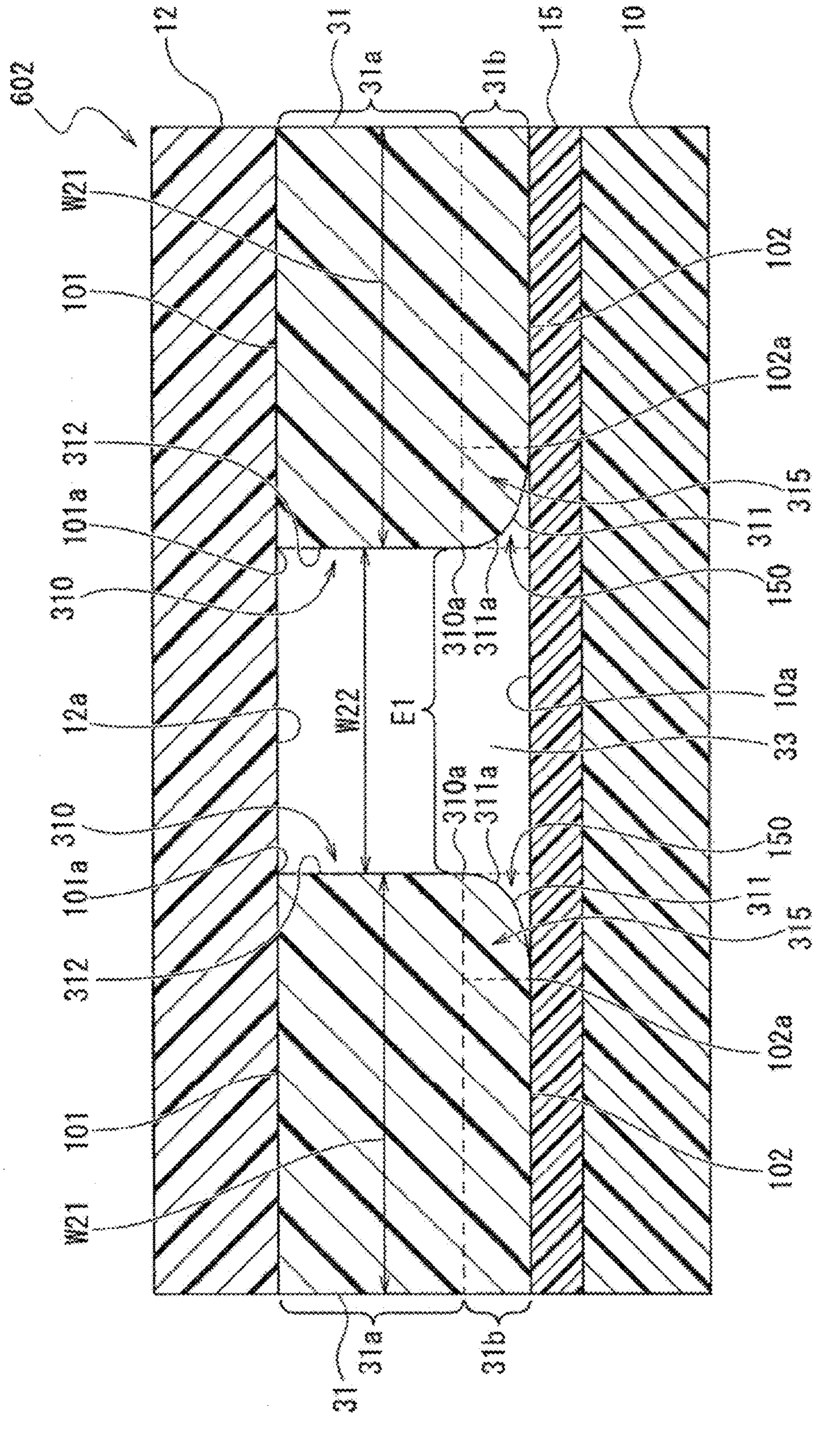
FIG. 11 is a schematic cross-sectional diagram illustrating an example configuration of a microfluidic chip according to a second modified example of the fourth embodiment the present invention.

Next, referring to FIG. 11, a configuration of a microfluidic chip 602 according to a second modified example of the present embodiment will be described. FIG. 11 is a schematic cross-sectional diagram illustrating an example configuration of the microfluidic chip 602 according to this modified example. The microfluidic chip 602 has a configuration in which an adhesive layer is additionally provided in the microfluidic chip 2 according to the second embodiment.

The microfluidic chip 602 includes a substrate 10, an adhesive layer 15 disposed on the substrate 10, a partition layer 31 that defines a fluidic channel portion 33 on the substrate 10, and a cover layer 12. That is, the microfluidic chip 602 differs from the microfluidic chip 2 according to the second embodiment in that the adhesive layer 15 is provided between the partition layer 31 and the substrate 10.

The adhesive layer 15 in this modified example is the same as the adhesive layer 15 in the microfluidic chip 6 according to the fourth embodiment described above, and the description thereof will be omitted. Providing the adhesive layer 15 can enhance the adhesion between the substrate 10 and a resin layer (for example, photosensitive resin layer), that is, the partition layer 31, in the microfluidic chip 602.

Third Modified Example

Figure 12:
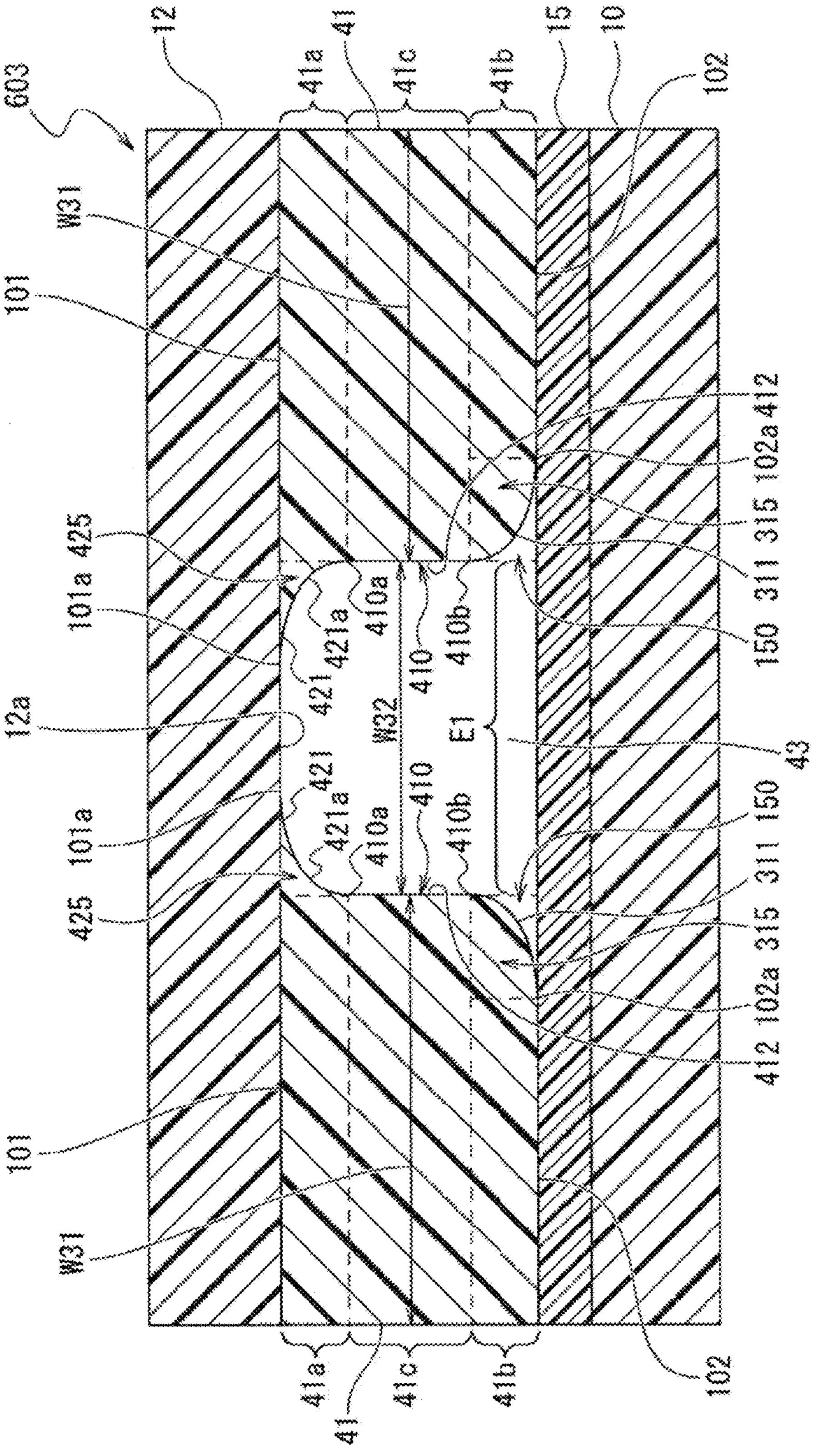
FIG. 12 is a schematic cross-sectional diagram illustrating an example configuration of a microfluidic chip according to a third modified example of the fourth embodiment of the present invention.

Next, referring to FIG. 12, a configuration of a microfluidic chip 603 according to a third modified example of the present embodiment will be described. FIG. 12 is a schematic cross-sectional diagram illustrating an example configuration of the microfluidic chip 603 according to this modified example. The microfluidic chip 603 has a configuration in which an adhesive layer is additionally provided in the microfluidic chip 201 according to the modified example of the second embodiment.

The microfluidic chip 603 includes a substrate 10, an adhesive layer 15 disposed on the substrate 10, a partition layer 41 that defines a fluidic channel portion 43 on the substrate 10, and a cover layer 12. That is, the microfluidic chip 603 differs from the microfluidic chip 201 according to the modified example of the second embodiment in that the adhesive layer 15 is provided between the partition layer 41 and the substrate 10. The adhesive layer 15 in this modified example is the same as the adhesive layer 15 in the microfluidic chip 6 according to the fourth embodiment described above, and the description thereof will be omitted. Providing the adhesive layer 15 can enhance the adhesion between the substrate 10 and a resin layer (for example, photosensitive resin layer), that is, the partition layer 41, in the microfluidic chip 603.

Fourth Modified Example

Figure 13:
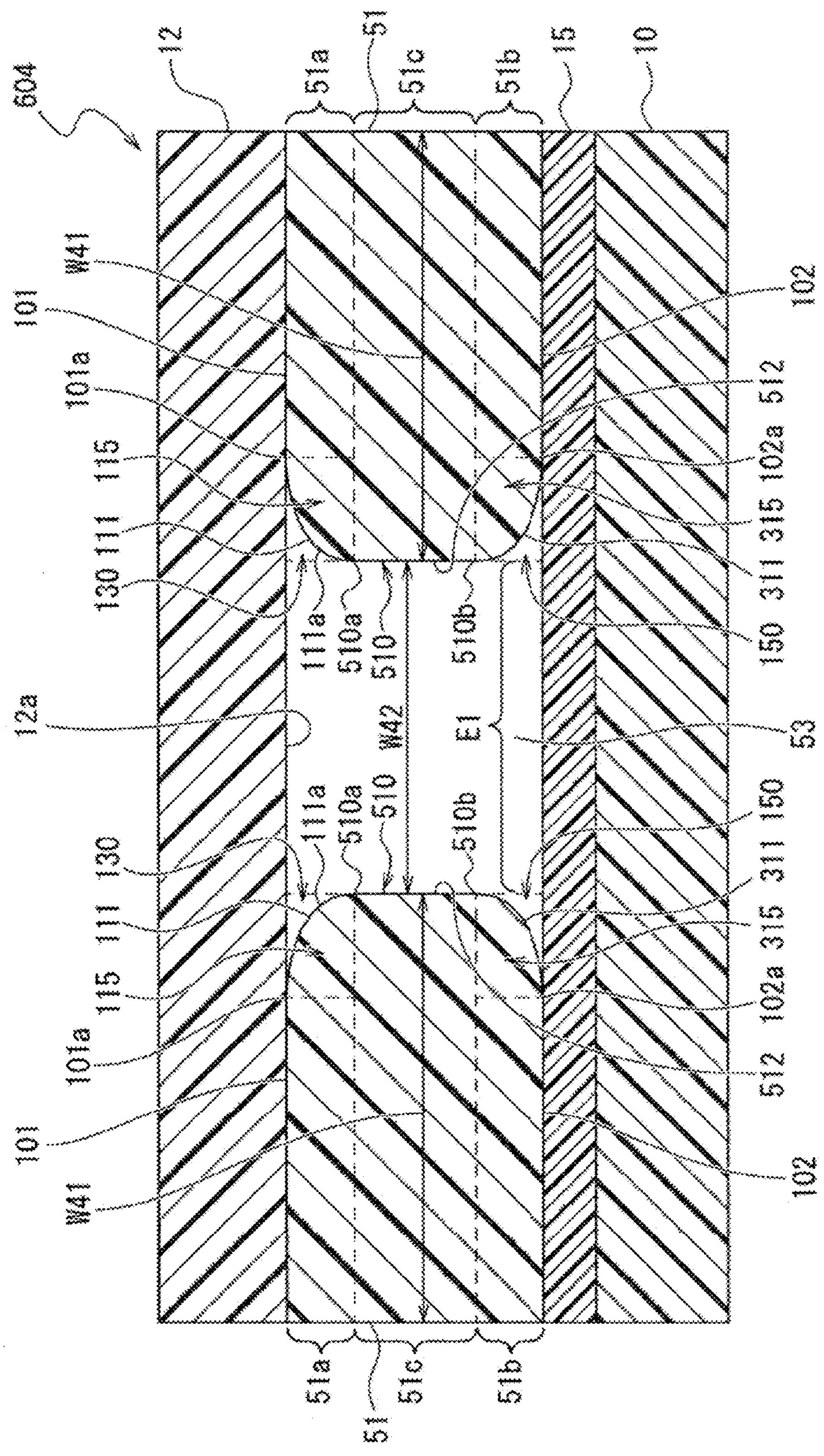
FIG. 13 is a schematic cross-sectional diagram illustrating an example configuration of a microfluidic chip according to a fourth modified example of the fourth embodiment the present invention.

Next, referring to FIG. 13, a configuration of a microfluidic chip 604 according to a fourth modified example of the present embodiment will be described. FIG. 12 is a schematic cross-sectional diagram illustrating an example configuration of the microfluidic chip 604 according to this modified example. The microfluidic chip 604 has a configuration in which an adhesive layer is additionally provided in the microfluidic chip 3 according to the third embodiment.

The microfluidic chip 604 includes a substrate 10, an adhesive layer 15 disposed on the substrate 10, a partition layer 51 that defines a fluidic channel portion 53 on the substrate 10, and a cover layer 12. That is, the microfluidic chip 604 differs from the microfluidic chip 3 according to the third embodiment in that the adhesive layer 15 is provided between the partition layer 51 and the substrate 10.

The adhesive layer 15 in this modified example is the same as the adhesive layer 15 in the microfluidic chip 6 according to the fourth embodiment described above, and the description thereof will be omitted. Providing the adhesive layer 15 can enhance the adhesion between the substrate 10 and a resin layer (for example, photosensitive resin layer), that is, the partition layer 51, in the microfluidic chip 604.

An embodiment of the present invention can be suitably used for microfluidic chips for research applications, diagnostic applications, testing, analysis, culture, and the like, which do not require complicated production processes to form a top lid, and methods of producing the same.

In recent years, technologies have been proposed in which micro reaction fields are formed by applying lithography processing or thick film processing technologies to enable testing in units of several microliters to several nanoliters. Technologies using such a micro reaction field are called μ-TAS (micro total analysis systems).

μ-TAS is applied to fields such as genetic testing, chromosome testing, cell testing and drug development, biotechnologies, testing of trace substances in the environment, investigation of breeding environments for agricultural products, genetic testing of agricultural products, and the like. The introduction of μ-TAS technologies brings significant effects such as automation, higher speed, higher accuracy, lower cost, speed, reduced environmental impact, and the like.

In μ-TAS, micrometer-sized fluidic channels (micro fluidic channels, micro channels) formed on a substrate are often used, and such a substrate is called a chip, microchip, microfluidic chip, or the like.

In microfluidic chips, a reaction solution flowing in a micro fluidic channel may contain air bubbles. Air bubbles may be contained, for example, due to entrainment of air bubbles during injection of a fluid such as a reaction solution into the microfluidic chip, boiling due to heating of the reaction solution, air entrainment due to non-uniform flow in the microfluidic channel, foaming from the reaction solution itself, or the like.

Such air bubbles cause instable fluid flow in the micro fluidic channel, inhibition of reaction of the reaction solution, and the like.

For example, in JP 2006-223118 A, a method of removing air bubbles from the micro fluidic channel is described, in which an air bubble separation unit is provided in a fluidic channel, and the air bubble separation unit has a mesh member that allows only air to pass through but not fluids so that air bubbles caused by air entrainment into microfluids are removed. Further, J P 2007-240461 A describes a method of producing a microfluidic chip by bonding components together with an adhesive.

In production of microfluidic chips, it is common to bond components together with an adhesive as described in JP 2007-240461 A. However, when the air bubble separation unit as described in JP 2006-223118 A is attached to the micro fluidic channel with an adhesive, an adhesive component may be eluted into a solution flowing in the micro fluidic channel, causing inhibition of reaction of the solution.

A microfluidic chip according to an embodiment of the present invention separates air bubbles in a micro fluidic channel into a specific region to improve stability of fluid flow and prevents an adhesive component from eluting into a solution in the fluidic channel to suppress inhibition of reaction of the solution, and a method of producing the microfluidic chip.

A microfluidic chip according to an aspect of the present invention is a microfluidic chip including: a fluidic channel; a first support member; a second support member; and a pair of partition members interposed between the first support member and the second support member to define the fluidic channel, wherein the partition member has a curved portion curved away from the first support member at an edge on the fluidic channel side of a contact surface in contact with the first support member, and the fluidic channel includes a bubble trapping region formed by the curved portion and a surface of the first support member on the fluidic channel side, the bubble trapping region trapping air bubbles in the fluidic channel.

A method of producing a microfluidic chip according to another aspect of the present invention includes: applying a resin to a substrate; exposing the applied resin to light; subjecting the exposed resin to development and cleaning to thereby form a partition member that defines a fluidic channel on the substrate; post-baking the partition member; and bonding a cover layer to a side of the partition member opposite to that facing the substrate, wherein excess resin on the substrate is removed by the development, whereby an upper curved portion curved in a convex shape at an edge on the fluidic channel side of a surface of the partition layer on a side opposite to that facing the substrate is formed.

A method of producing a microfluidic chip according to another aspect of the present invention includes: applying a resin to a substrate; exposing the applied resin to light; subjecting the exposed resin to development and cleaning to thereby form a partition member that defines a fluidic channel on the substrate; post-baking the partition member; and bonding a cover layer to a side of the partition member opposite to that facing the substrate, wherein excess resin on the substrate is removed by the development, whereby a curved portion curved in a convex shape at an edge on the fluidic channel side of a surface of the partition layer in contact with the substrate is formed.

A microfluidic chip according to an embodiment of the present invention separates air bubbles in a micro fluidic channel into a specific region to improve stability of fluid flow and prevents an adhesive component from eluting into a solution in the fluidic channel to suppress inhibition of reaction of the solution.

Obviously, numerous modifications and variations of the present invention are possible in light of the above teachings. It is therefore to be understood that within the scope of the appended claims, the invention may be practiced otherwise than as specifically described herein.

The invention claimed is:

1. A microfluidic chip, comprising:

a first support member;

a second support member; and a plurality of partition members interposed between the first support member and the second support member such that the first support member, the second support member and the partition members form a fluidic channel, wherein each of the partition members has an curved portion curved away from the first support member at an edge on a fluidic channel side of a contact surface in contact with the first support member such that the curved portion and a surface of the first support member on the fluidic channel side form a bubble trapping region configured to trap air bubbles in the fluidic channel.

2. The microfluidic chip according to claim 1, wherein the fluidic channel has a width which increases toward the first support member in a region formed by the curved portion of the partition member and is constant in a region formed by a portion of the partition member other than the curved portion.

3. The microfluidic chip according to claim 1, wherein each of the partition members includes an extension portion which extends in a transverse direction of the fluidic channel along a surface of the second support member, the partition member having a width increasing toward the second support member in cross-sectional view.

4. The microfluidic chip according to claim 3, wherein the extension portion has a curved surface curved in a concave shape in cross-sectional view.

5. The microfluidic chip according to claim 3, wherein the width of the fluidic channel decreases toward the second support member in a region formed by the extension portion of each of the partition members.

6. The microfluidic chip according to claim 1, wherein each of the partition members has a second curved portion curved in a direction away from the second support member at an edge on the fluidic channel side of a contact surface in contact with the second support member such that the second curved portion and a surface of the second support member on the fluidic channel side form a second bubble trapping region configured to trap air bubbles in the fluidic channel.

7. The microfluidic chip according to claim 6, wherein the fluidic channel has a width which increases toward the second support member in a region formed by the second curved portion of each of the partition members.

8. The microfluidic chip according to claim 1, wherein the first support member is a cover layer positioned on an upper side of the partition member and covering an upper part of the fluidic channel, and the second support member is a substrate positioned on a bottom side of the partition member and forming a bottom of the fluidic channel.

9. The microfluidic chip according to claim 1, wherein the first support member is a substrate positioned on a bottom side of the partition member and forming a bottom of the fluidic channel, and the second support member is a cover layer positioned on an upper side of the partition member and covering an upper part of the fluidic channel.

10. The microfluidic chip according to claim 8, further comprising:

an adhesive layer formed between the partition member and the substrate.

11. The microfluidic chip according to claim 1, wherein each of the partition members comprises resin material comprising a photosensitive resin photosensitive to light having a wavelength in a range of 190 nm 400 nm in an ultraviolet light region.

12. The microfluidic chip according to claim 2, wherein each of the partition members includes an extension portion which extends in a transverse direction of the fluidic channel along a surface of the second support member, the partition member having a width increasing toward the second support member in cross-sectional view.

13. The microfluidic chip according to claim 12, wherein the extension portion has a curved surface curved in a concave shape in cross-sectional view.

14. The microfluidic chip according to claim 12, wherein the width of the fluidic channel decreases toward the second support member in a region formed by the extension portion of each of the partition members.

15. The microfluidic chip according to claim 2, wherein each of the partition members has a second curved portion curved in a direction away from the second support member at an edge on the fluidic channel side of a contact surface in contact with the second support member such that the second curved portion and a surface of the second support member on the fluidic channel side form a second bubble trapping region configured to trap air bubbles in the fluidic channel.

16. A method of producing a microfluidic chip, comprising:

applying a resin to a substrate;

exposing the resin applied to the substrate to light;

subjecting the resin to development and cleaning such that a plurality of partition members and a fluidic channel are formed on the substrate;

post-baking the partition members formed on the substrate; and bonding a cover layer to a side of the partition members on an opposite side with respect to the substrate, wherein the subjecting the resin to the development and cleaning includes removing excess resin on the substrate such that an upper curved portion curved in a convex shape is formed at an edge on a fluidic channel side of a surface of each of the partition members on an opposite side with respect to the substrate.

17. The method of producing a microfluidic chip according to claim 16, wherein the subjecting the resin to the development and cleaning includes forming each of the partition members in a shape in which a width increases toward the substrate in cross-sectional view on the substrate side of the partition member.

18. The method of producing a microfluidic chip according to claim 16, wherein the subjecting the resin to the development and cleaning includes forming a lower curved portion curved in a convex shape at an edge on the fluidic channel side of a surface of each of the partition members in contact with the substrate.

19. A method of producing a microfluidic chip, comprising:

applying a resin to a substrate;

exposing the resin applied to the substrate to light;

subjecting the resin to development and cleaning such that a plurality of partition members and a fluidic channel are formed on the substrate;

post-baking the partition members formed on the substrate; and bonding a cover layer to a side of the partition members on an opposite side with respect to the substrate, wherein the subjecting the resin to the development and cleaning includes removing excess resin on the substrate such that a curved portion curved in a convex shape is formed at an edge on a fluidic channel side of a surface of each of the partition members in contact with the substrate.

20. The method of producing a microfluidic chip according to claim 19, wherein the exposing the resin to the light includes exposing the resin comprising a photosensitive resin to light having a wavelength in a range of 250 nm to 350 nm in an ultraviolet light range, and the subjecting the resin to the development and cleaning includes forming each of the partition members in a shape in which a width increases toward the cover layer in cross-sectional view on a side of the partition member in an opposite side with respect to the substrate.

* * * * *